US006484584B2

(12) United States Patent
Johnson et al.

(10) Patent No.: US 6,484,584 B2
(45) Date of Patent: Nov. 26, 2002

(54) METHOD FOR THE CONCURRENT ULTRASONIC INSPECTION OF PARTIALLY COMPLETED WELDS

(75) Inventors: John A. Johnson, Idaho Falls, ID (US); Eric D. Larsen, Idaho Falls, ID (US); Karen S. Miller, Idaho Falls, ID (US); Herschel B. Smartt, Idaho Falls, ID (US); Timothy R. McJunkin, Idaho Falls, ID (US)

(73) Assignee: Bechtel BWXT Idaho, LLC, Idaho Falls, ID (US)

(*) Notice: Subject to any disclaimer, the term of this patent is extended or adjusted under 35 U.S.C. 154(b) by 101 days.

(21) Appl. No.: 09/741,203

(22) Filed: Dec. 19, 2000

(65) Prior Publication Data

US 2001/0052264 A1 Dec. 20, 2001

Related U.S. Application Data

(63) Continuation-in-part of application No. 09/583,632, filed on May 31, 2000, now Pat. No. 6,365,873.

(51) Int. Cl.[7] .......................... G01N 29/10; G01N 29/26
(52) U.S. Cl. ............................... 73/624; 73/625; 73/628
(58) Field of Search .......................... 73/627, 628, 629, 73/618, 619, 620, 621, 622, 624, 625; 219/124.34, 130.21, 137.71

(56) References Cited

U.S. PATENT DOCUMENTS

| | | | | |
|---|---|---|---|---|
| 3,575,042 A | * | 4/1971 | Lovelace et al. | 73/609 |
| 3,575,044 A | * | 4/1971 | Gibbs et al. | 228/104 |
| 3,585,851 A | * | 6/1971 | Walther | 73/624 |
| 3,648,009 A | * | 3/1972 | Steigerwald | 219/110 |
| 3,888,114 A | * | 6/1975 | Adams et al. | 73/628 |
| 4,294,118 A | * | 10/1981 | Shiraiwa et al. | 73/620 |
| 4,588,873 A | * | 5/1986 | Fenn et al. | 219/124.34 |
| 4,712,722 A | * | 12/1987 | Hood et al. | 228/104 |
| 6,125,705 A | * | 10/2000 | Johnson | 73/598 |
| 6,365,873 B1 | * | 4/2002 | Smartt et al. | 219/130.01 |

OTHER PUBLICATIONS

Passi, G., et al, "High–reliability manual ultrasonic inspection," *INSIGHT Non–Destructive Testing and Condition Monitoring*, vol. 41 No. 4, Apr. 1999, pp. 225–231.

* cited by examiner

*Primary Examiner*—Hezron Williams
*Assistant Examiner*—Rose M. Miller
(74) *Attorney, Agent, or Firm*—Wells StJohn Roberts Gregory & Matkin

(57) ABSTRACT

A method for the concurrent ultrasonic inspection of partially completed welds is disclosed and which includes providing a pair of transducers which are individually positioned on the opposite sides of a partially completed weld to be inspected; moving the transducers along the length of and laterally inwardly and outwardly relative to the partially completed weld; pulsing the respective transducers to produce an ultrasonic signal which passes through or is reflected from the partially completed weld; receiving from the respective transducers ultrasonic signals which pass through or are reflected from the partially completed welds; and analyzing the ultrasonic signal which has passed through or is reflected from the partially completed weld to determine the presence of any weld defects.

28 Claims, 17 Drawing Sheets

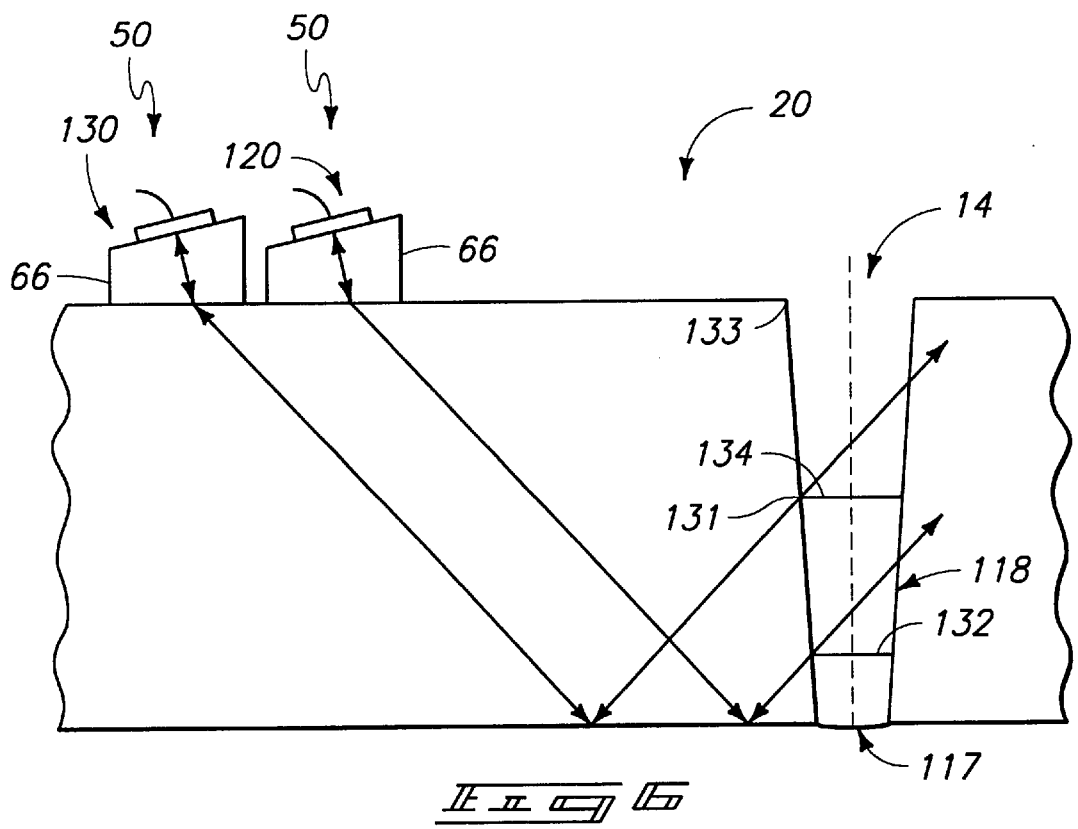
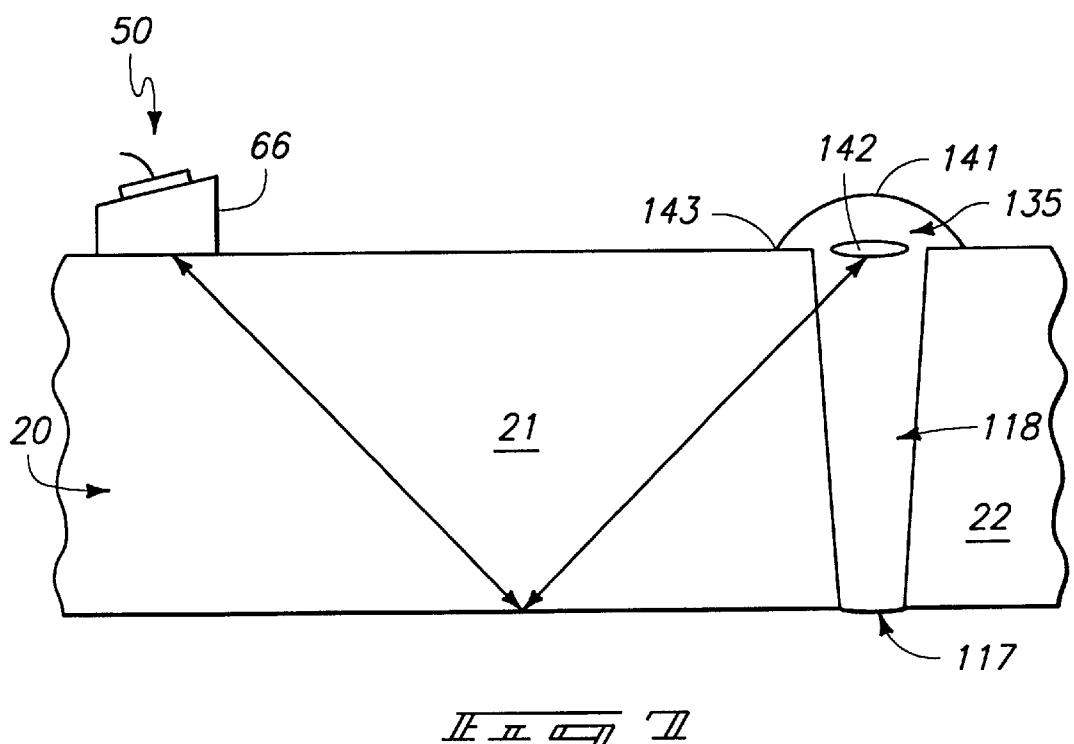

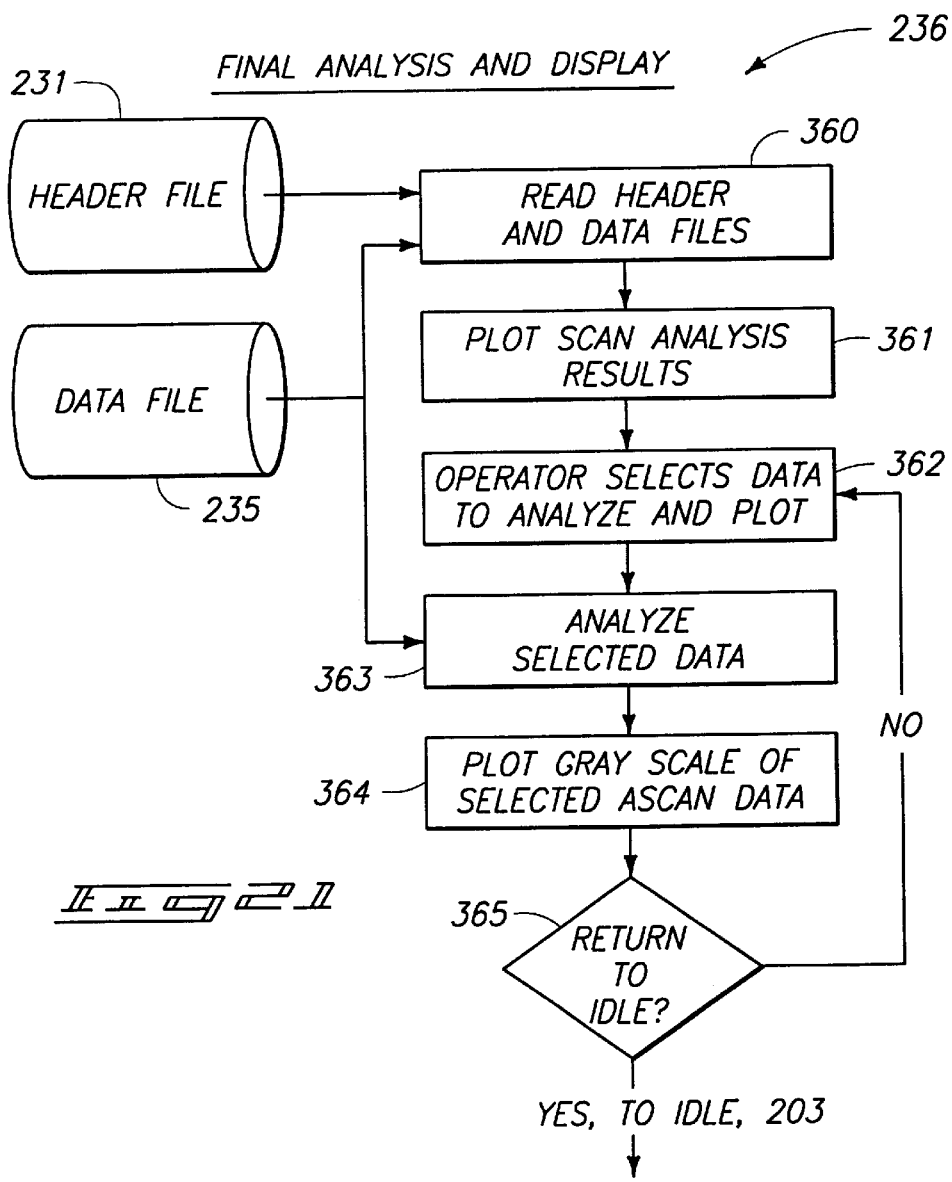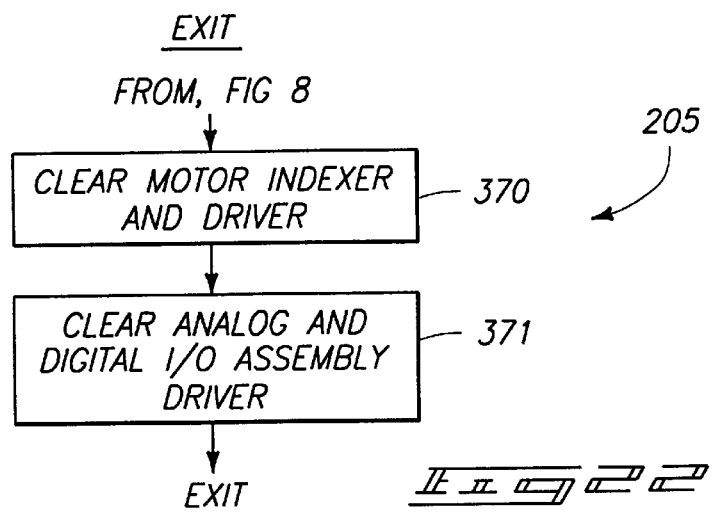

METHOD FOR THE CONCURRENT ULTRASONIC INSPECTION OF PARTIALLY COMPLETED WELDS

RELATED APPLICATION

This application is a continuation-in-part and claims priority from U.S. patent application Ser. No. 09/583,632 filed May 31, 2000 and now U.S. Pat. No. 6,365,873B1 and which is incorporated by reference herein.

CONTRACTUAL ORIGIN OF THE INVENTION

This invention was made with United States Government support under Contract No. DE-AC07-94ID13223, now Contract No. DE-AC07-99ID13727 awarded by the United States Department of Energy. The United States Government has certain rights in the invention.

FIELD OF THE INVENTION

The present invention relates to a method which facilitates the concurrent non-destructive evaluation of partially completed welds.

BACKGROUND OF THE INVENTION

Thick sectional welds are usually made in several passes. In this regard, it should be understood that the area between two adjacent parts to be joined is filled up a portion at a time. In testing of such thick sectional welds, ultrasonic sensors and other non-destructive evaluation methods are often used to inspect same. However, under most operational circumstances, these inspections have been done heretofore at some time period after the welding has been completed and the weld has cooled down. It has long been known that when welding defects are detected on a pass-by-pass basis, they can be easily repaired before being covered by the welding material laid down by subsequent welding passes. Thus, for example, a defect in the root pass can be repaired easily and economically without grinding out all the welding metal from the later passes. This welding method contrasts with inspecting a completed weld because a significant amount of weld material may have to be subsequently removed to reach the welding defect. Still further, and as discussed in U.S. Pat. No. 4,712,722, a significant economic and productivity advantage can be obtained if welding flaws can be substantially concurrently detected and repaired on a pass-by-pass basis.

As noted further in our application Ser. No. 09/583,632 from which we claim priority, it has been discovered that for inspection of welds to be accurate, the movement of ultrasonic sensors must be synchronized within small tolerance parameters.

In view of the foregoing, it would be highly desirable to provide a method for the concurrent ultrasonic inspection of partially completed welds which achieves the benefits to be derived from the aforementioned technology but which avoids the detriments individually associated therewith.

SUMMARY OF THE INVENTION

Therefore, one aspect of the present invention is to provide an improved method for the concurrent ultrasonic inspection of partially completed welds.

Another aspect of the present invention is to provide a method for the concurrent ultrasonic inspection of partially completed welds which includes the steps of providing a pair of transducers which are individually positioned on the opposite sides of a partially completed weld to be inspected; moving the transducers along the length of and laterally inwardly and outwardly relative to the partially completed weld; pulsing the respective transducers to produce an ultrasonic signal which passes through or is reflected from the partially completed weld; receiving from the respective transducers ultrasonic signals which pass through or are reflected from the partially completed weld; and analyzing the ultrasonic signal which is passed through or is reflected from the partially completed weld to determine the presence of any weld defects.

Another aspect of the present invention is to provide a method for the concurrent ultrasonic inspection of partially completed welds which includes providing a pair of transducers which are individually positioned on the opposite sides of a partially completed weld which is to be inspected; providing a pair of motors which are individually disposed in driving relation relative to each of the transducers; providing a controlling computer having executable programming for selectively controlling the movement of each of the motors; energizing the respective motors with a controlling computer to cause the respective transducers to travel in a predetermined synchronous pattern of motion; pulsing the respective transducers with a controlling computer to produce an ultrasonic signal which is reflected from or which passes through the weld which is being inspected while the transducers are being moved in the predetermined synchronous pattern of motion; and analyzing the ultrasonic signal which is reflected from or which passes through the partially completed weld by the controlling computer to determine the presence of any weld defects.

Still further, another aspect of the present invention is to provide a method for the concurrent ultrasonic inspection of partially completed welds wherein the method employs a controlling computer which includes a pair of pulser/receivers which are controlled by the controlling computer, and which are individually electrically coupled with each of the transducers; an analog to digital converter controlled by the controlling computer and which receives the ultrasonic signal which passes through or is reflected from the partially completed weld being inspected; and an analog and digital input/output assembly controlled by the controlling computer and which is coupled in signal transmitting relation relative to the pair of pulser/receivers and which generates a signal causing the pair of pulser/receivers to produce a pulse, and wherein the signal further causes the analog and digital converter to receive the ultrasonic signal.

Still another aspect of the present invention relates to a method for the concurrent ultrasonic inspection of partially completed welds wherein the controlling computer energizes each of the motors in a manner to cause the substantially synchronous movement of each of the transducers along a predetermined path of travel.

Yet still further, another aspect of the present invention relates to a method for the concurrent ultrasonic inspection of partially completed welds wherein the computer, having executable programming, coordinates the pulsing of the respective transducers during the movement of the respective transducers along the path of travel, and wherein, the controlling computer determines the predetermined locations.

Another aspect of the present invention is to provide a method for the concurrent ultrasonic inspection of partially completed welds wherein the step of analyzing the ultrasonic signal occurs following the completion of the movement of the respective transducers.

These and other aspects of the present invention will be discussed hereinafter.

BRIEF DESCRIPTION OF THE DRAWINGS

Preferred embodiments of the invention are described below with reference to the following accompanying drawings which are briefly described in the paragraphs which follow:

FIG. 6 is a greatly simplified transverse, vertical sectional view taken through a transducer positioned in alternative locations on one side of a weld being formed.

FIG. 7 is a greatly simplified transverse, vertical sectional view taken through a transducer positioned on one side of a weld which has been completed, and which has a defect formed in same.

FIG. 21 is a flow diagram illustrating certain methodical aspects of the present invention.

FIG. 22 is a flow diagram illustrating certain methodical aspects of the present invention.

DETAILED DESCRIPTION

This disclosure of the invention is submitted in furtherance of the constitutional purposes of the U.S. Patent Laws "to promote the progress of science and useful arts" (Article 1, Section 8).

The method for the concurrent ultrasonic inspection of partially completed welds is best understood by a study of FIG. 1, and FIGS. 8 through 22 respectively.

Figure 1:
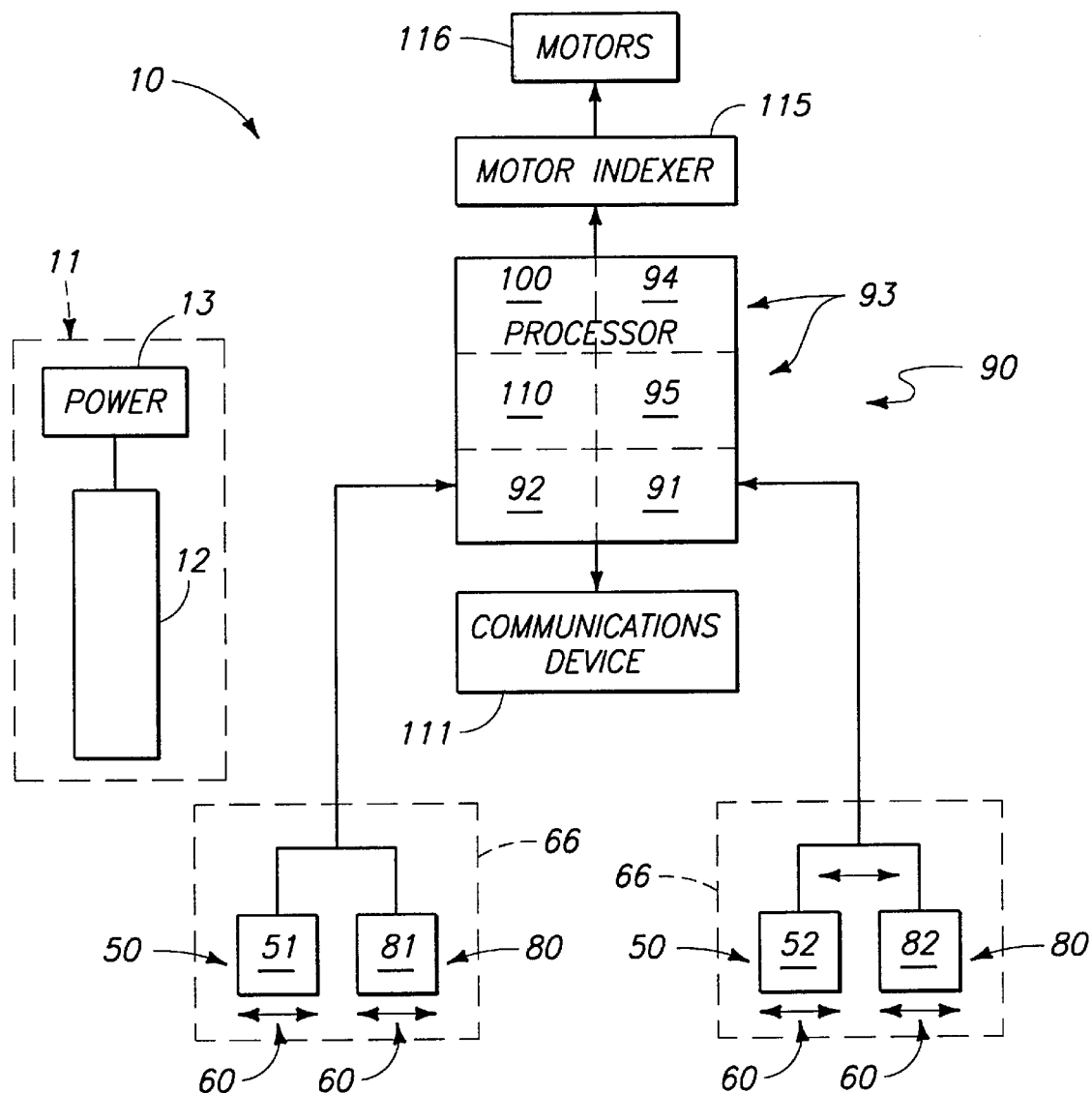
FIG. 1 is a greatly simplified schematic diagram of the present invention.

As shown in FIG. 1, an apparatus 10 which implements the present method is shown in a very simplified schematic diagram. In this regard, the apparatus 10, which implements the present method, includes an automated movable welder which is schematically indicated by the numeral 11. Automated movable welders are familiar to those who are skilled in the art and, therefore, a detailed discussion of these devices is neither warranted nor necessary for an understanding of the invention. However, it should be appreciated that the automated movable welder is operable to be attached to a given object which is to be welded. The automated welder then moves repeatedly along a prescribed path of travel to achieve a given welding objective. As seen in FIG. 1, the automated movable welder includes a welding head 12 which has a power supply 13 connected thereto. The power supply 13 supplies the electricity necessary to perform the welding activity. As seen most clearly by reference to FIG. 2, the welding head 12 is shown in a given position to achieve a desired welding objective with respect to a partially completed weld which is shown generally by the numeral 14. The welding head 12 is movable along a given path of travel which is generally indicated by the numeral 15. The automated movable welder 11 is operable to weld a given substrate designated by the numeral 20. The substrate comprises first and second sections 21 and 22, respectively, and which are positioned in juxtaposed relation one to the other. Each of the sections 21 and 22, to be welded, includes a top surface 23, a bottom surface 24 and a side wall 25. A partially completed weld 14 has opposite sides 26 and 27 respectively.

Figure 3:
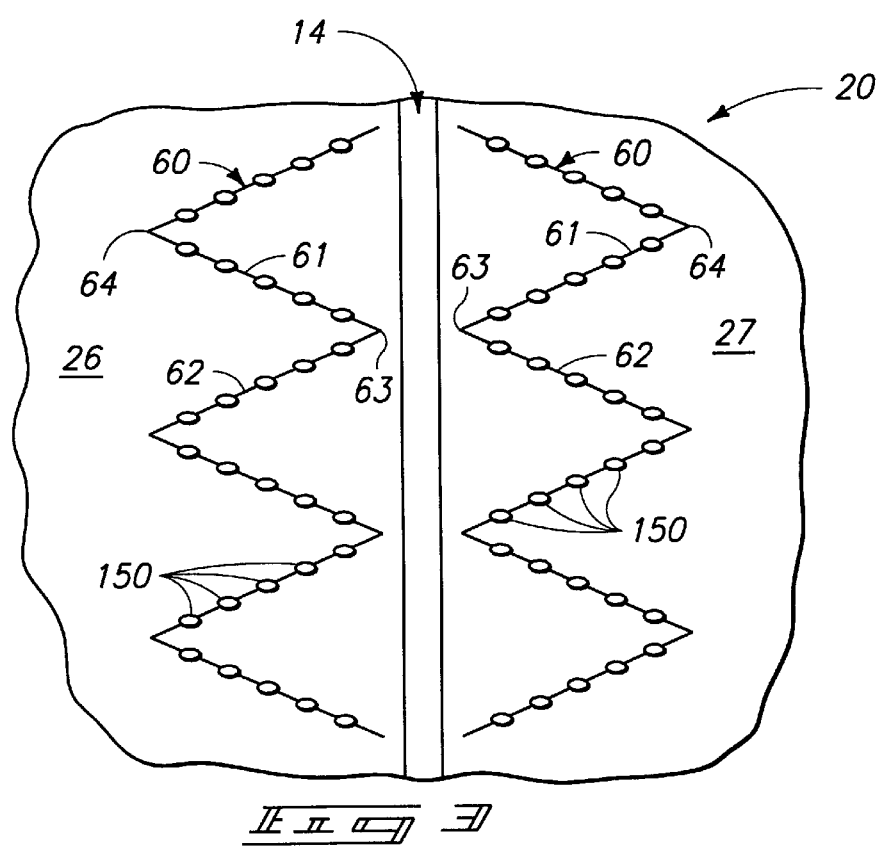
FIG. 3 is a greatly simplified schematic, plan view of the path of travel of the transducers relative to the side of a weld.
Figure 4:
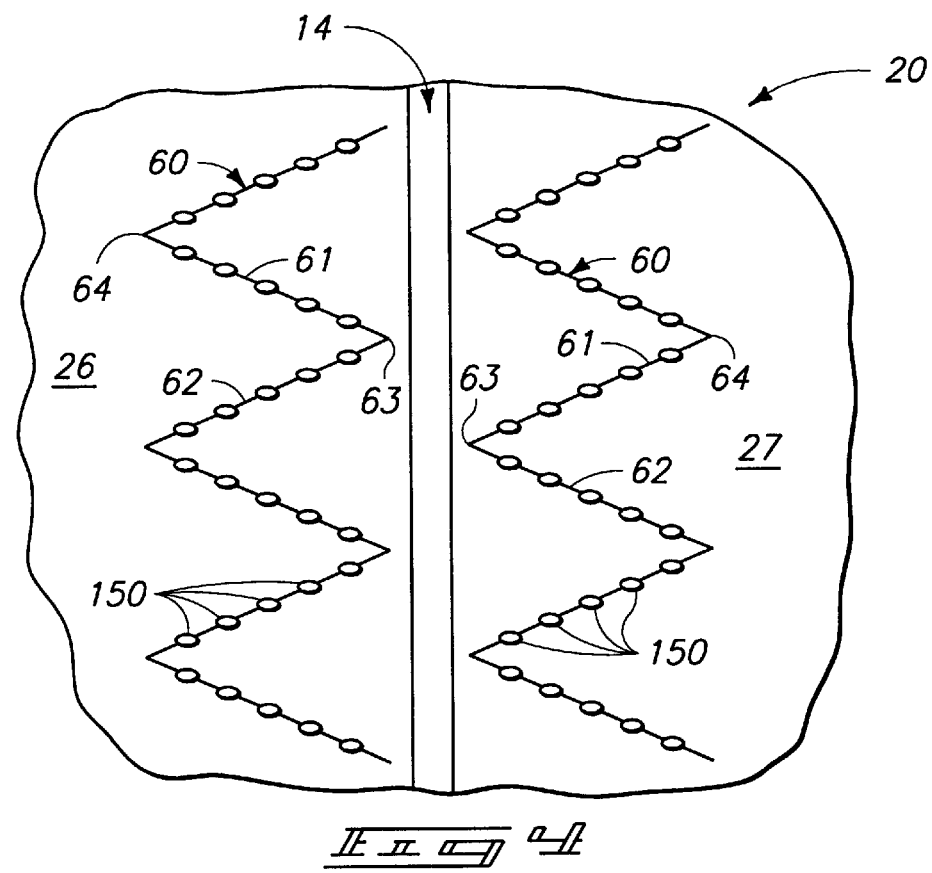
FIG. 4 is a second, greatly simplified view of an alternative path of movement of a pair of transducers relative to the side of a weld.

As seen in FIGS. 1 and 2 and 5 through 7, respectively, the apparatus 10 which implements the method of the present invention includes an ultrasonic signal generator 50 which is mounted on the automated movable welder 11 and which generates an ultrasonic signal which is directed towards one side of the partially completed weld 14. The ultrasonic signal generator as seen in our pending application from which we claim priority, is mounted in spaced trailing relation relative to the path of movement of the automated welder 11. As seen in FIGS. 2 and 5 through 7, the ultrasonic signal generator 50 may include first and second ultrasonic signal generators 51 and 52 which are mounted on the opposite sides 26 and 27 of the partially completed weld 14. As seen in FIGS. 3 and 4, the ultrasonic signal generators 51 and 52 are movable along a plurality of paths of travel 60 designated by the numeral 60. As can be seen in FIGS. 3 and 4, the respective paths of travel 60 on the opposite sides of the partially complete weld 14 are substantially synchronous, and, as illustrated, the individual paths assume in one form a substantially sinusoidal shape when viewed from above, and along the length of the partially completed weld 14. The generally lateral paths 60 are modified as shown in FIG. 3 and in FIG. 4 by the path of travel 15 of the weld head 11 as it moves in the direction of the partially completed weld 14. As seen in FIG. 3, the individual paths of travel can be synchronous and out of phase, or as seen in FIG. 4, can be substantially synchronous and in phase depending upon the type of weld defect being detected by the present method. Each path of travel includes first and second components 61 and 62, respectively. Each path of travel is defined between a first and second position 63 and 64. The paths of travel 60 are generally laterally inwardly and outwardly relative to the side of the partially completed weld 14.

It should be understood that in certain forms of the invention, a pair of ultrasonic signal generators or transducers 50 may be mounted on the opposite sides of the weld. These respective pairs of transducers 50 may have individual paths of travel which are substantially coaxially aligned or further may be additionally independently movable in a direction which is laterally and outwardly positioned relative to the orientation of the partially completed weld 14.

In the present invention, as shown by the apparatus 10 as depicted in FIG. 1 and which implements the. method of the present invention, the invention may be implemented by utilizing discreet ultrasonic signal generators 50, or in the alternative, by utilizing a transducer 66 which performs both functions of an ultrasonic signal generator 50, and an ultrasonic signal receiver 80 as will be described hereinafter.

Figure 5:
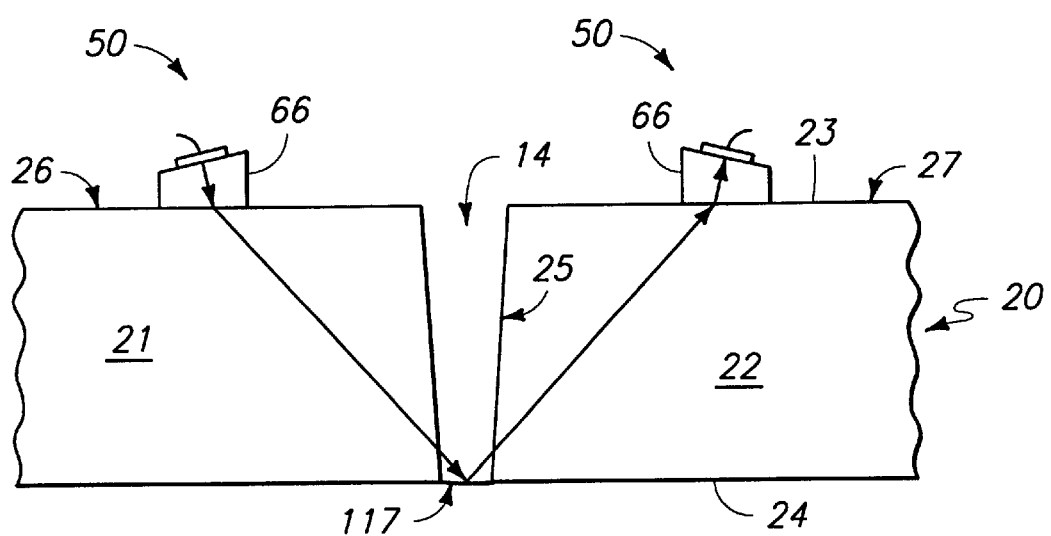
FIG. 5 is a greatly simplified, transverse, vertical sectional view taken through two transducers positioned on the opposite sides of a weld being formed.

As best seen in FIG. 1, the apparatus which implements the method for the concurrent ultrasonic inspection of partially completed weld 14 includes an ultrasonic signal receiver 80 which is designated generally by the numeral 80. As seen in FIGS. 2, and 5 through 7, the ultrasonic signal receiver 80 may be incorporated into a structure of a conventional transducer 66 as earlier described, or may comprise individual first or second ultrasonic signal receivers 81 and 82 respectively. As was described above with respect to the paths of travel 60 of the ultrasonic signal generator 50, it should be appreciated that the ultrasonic signal receiver 80 moves along substantially the same courses of travel. When mounted on the automated movable welder 11, the ultrasonic signal receiver 80 detects ultrasonic signals which are transmitted by the ultrasonic signal generator 50 and which are reflected, or pass through the partially completed weld 14, such as seen in FIGS. 5 and 6, for example. As seen in FIG. 1, the apparatus 10 which implements the method for the concurrent ultrasonic inspection of partially completed welds, is provided with an automated signal processor or controlling computer generally indicated by the numeral 90. The controlling computer or signal processor 90 couples the ultrasonic signal generator 50 and receiver 80 together. The controlling computer 90 further has executable programming (FIGS. 8–22) for selectively controlling the movement of the respective transducers 66 as will be discussed in greater detail hereinafter. The controlling computer or automated processor 90 includes a control assembly 92 which is coupled with the automated welder 11, and an analysis assembly 91. The control assembly 92, in combination with the analysis assembly 91, starts and stops the operation of the automated movable welder 11 when the number of welding flaws reach a predetermined number or given size. Further, the control assembly 92 controls the generation of ultrasonic signals that are being delivered to the weld to be inspected. In operation, and as best appreciated by the study of FIG. 1, the analysis assembly 91 receives several ultrasonic signals from the respective ultrasonic signal receivers 80. These signals are subsequently correlated and analyzed by the analysis assembly 91 to confirm the presence, location and type of a given welding flaw. This aspect of the present invention will be discussed in the methodology, which follows.

Still further the controlling computer 90 includes a pulser/receiver generally indicated by the numeral 93. The pulser/receiver 93 includes a first pulser/receiver 94 and a second pulser/receiver 95. Still, further, the controlling computer 90 includes an analog to digital converter 100. The analog to digital converter 100 is controlled by the controlling computer 90 and receives the ultrasonic signals which passes through, or is reflected from the partially completed weld being inspected 14. It should be understood that the pair of pulser/receivers 93 are electrically coupled by the controlling computer 90 with the respective transducers 66. The controlling computer 90 also includes an analog and digital input/output assembly 110. The controlling computer 90 controls the analog and digital input/output assembly 110 such that it is coupled in signal transmitting relation relative to the pair of pulser/receivers 93. This analog and digital input/output assembly 110 generates a signal causing the pair of pulser/receivers 93 to produce a pulse, and wherein the signal further causes the analog to digital converter 100 to receive the ultrasonic signal generated by the respective transducers 66.

A communication device 111 is coupled with the analysis assembly 91 and identifies the location of each welding flaw which exceeds predetermined parameters. The communications device 111 can comprise a number of different assemblies, but as a general matter, the communications device 111 provides machine readable indicia which identifies the type and location of the welding flaw such that an operator can then perform corrective action to remedy the given welding flaw before the automated welder 11 makes a subsequent pass through the same physical location. Still further, and as seen in FIG. 1, the controlling computer 90 is coupled by means of a motor indexer 115 with at least one motor 116 which controls the position of the ultrasonic signal generator 50 or signal receiver 80 along the respective paths of travel 60 earlier described to achieve the benefits which will be discussed below. It should be understood that the motor indexer 115 directs the movement of one or more of the motors 116, and when two or more motors 116 are used, the motor indexer 115 directs the movement of one of the motors 116, and the other of the motors 116 by way of the executable program (which will be discussed below) substantially follows and matches the position of the motor being controlled by the executable program 200 which is being executed by the controlling computer 90. It should be understood that the motor(s) 116 provides a means by which the respective ultrasonic signal generators 50 and the receivers 80 can be adjusted to follow the path 60 during on-going welding operations. As noted above, the motor indexer 115 is responsive to the controlling computer 90, and the controlling computer 90 has an executable program 200 which is downloadable to the motor indexer 115 to control the motion of the respective motors 116.

In the present invention, it is well known that when an ultrasonic sound wave travels in a solid medium and impinges on a plane surface, two reflected waves can be produced. One wave is reflected at the same angle as the incident wave and has the same mode [either longitudinal or shear] and the other wave which has been termed the mode converted wave is of the other mode and reflects at a different angle. For example, an incident shear wave is divided into a reflected shear wave and a reflected longitudinal wave. In addition, two wave modes may also be transmitted into the medium onto the other side of the plane. The two waves travel at different speeds and these determine the angle of reflection of the mode converted wave. It should be recognized that one of the perceived shortcomings of the prior art practices has been the identification and confirmation of welding flaws which are present in partially completed welds having different geometries. In U.S. Pat. No. 6,125,705 ('705) which is incorporated by reference herein, the inventors show possible ultrasonic beam positions and angles for inspecting partially completed narrow groove welds by utilizing the apparatus 10 of the present invention. As will be recognized and as was discussed in '705, the movement of the respective ultrasonic signal generator 50 and ultrasonic signal receivers 80 to discreet positions which are substantially laterally outwardly positioned relative to the partially completed welds 14 permits the invention to detect such defects as lack of side wall fusion [LOF] defects in a partially completed narrow groove weld 14. Still further the same application discloses the use of ultrasonic signals in a technique which has been termed "pitch-catch" ultrasonics. Still further, the same application discloses the use of ultrasonic signals in a technique which has been termed "pulse-echo" ultrasonics. By utilizing these techniques and analyzing the signals that are produced, different regions of the weld can be inspected. The precise positioning, however, of the transducer 66 in order to achieve this inspection must be precisely controlled and is achieved by the executable computer programming 200 resident in the controlling computer 90 which will be discussed below.

As discussed briefly above, the executable programming 200 utilized by the controlling computer 90 provides a means by which the various ultrasonic signals which are transmitted or received are analyzed to determine the presence of welding flaws at given locations in the partially completed weld 14. Before proceeding to a discussion of the programming a general understanding of the analysis of various portions of the weld geometry are in order.

Root Pass

Flaws that occur from time to time in the root pass 117 include lack of penetration [LOP], centerline hot cracks, and porosity. For detection of defects in the root pass 117, the transducers 66 move substantially synchronously and out-of-phase, as seen in FIG. 3. In the alternative the transducers 66 may move substantially in-phase and synchronously as seen in FIG. 4. When moving in-phase, the separation between the transducers 66 is substantially constant and is set such that the pitch-catch signal from one transducer which reflects off the inside or bottom surface 24 of the substrate to be welded 20 and arrives at the other transducer such that transmission of the signal is optimized. The amplitude of the pitch-catch ultrasonic signal is important to the resulting analysis of the ultrasonic signal received. Under most circumstances the amplitude of this ultrasonic signal is large. However, the presence of a welding flaw can reduce the amplitude. In the case of a crack that may be present, the ultrasonic beam is blocked by the crack. Further, in the case of LOP the reflection at the inside or bottom surface 24 of the substrate 20 is disrupted. Still further in those instances where the welding defect is porosity the amplitude is reduced by scattering of the ultrasonic beam caused by the porosity. It should be understood that if the amplitude of the pitch-catch ultrasonic signal is reduced, the pulseecho signals are examined to determine if a flaw is present during the analysis of the ultrasonic signal. In the event that the transducers 66 are moved in an out-of-phase pattern as seen in FIG. 3, the separation between the transducers vary but the pitch-catch ultrasonic signal from one transducer reflecting off the substrate 20 and received at the other transducer is best at one position. As seen in FIG. 5, an ultrasonic signal is generated, and is reflected off the root pass 117 and is thereafter received in a transducer 66 located on the opposite side 27 of the partially completed weld 14. In addition to the crack, lack of penetration (LOP) and porosity defects which may be detected by the method of the present invention, other causes of reduced ultrasonic pitch-catch signals can include root roughness or other mismatch. The pitch-catch ultrasonic signal in the case of a mismatch has a somewhat distinct shape that can be recognized by analysis assembly 91. In the case of roughness at the root or on the bottom surface 24 of the substrate 20 to be welded, the resulting reflected ultrasonic signals are generally very small and do not have the same distinct pattern as may be produced if a welding defect such as porosity is present. In the subsequent analysis of ultrasonic signals reflected from or passing through the root pass 117 region, the amplitude of the pitch-catch signal is first examined, then the pulse-echo ultrasonic signals are examined.

Hot And Fill Passes

Welding flaws that may occur in these portions 118 of a partially completed weld 14, and which can be subsequently detected by the method of the present invention may include lack of side wall fusion [LOF] and porosity. During this analysis, and under most circumstances, the pulse/echo ultrasonic signals are the only signals used to detect welding flaws. In view of inherent geometric restrictions, the transducers 66 are moved substantially synchronously and out of phase as shown in FIG. 3 for this analysis. It should be understood that a pitch-catch ultrasonic signal is acquired during this analysis when the transducers 66 are spaced nearest one to the other. It has also been found that this ultrasonic signal may be useful for calibrating the ultrasound speed as a function of temperature in the root pass region 117. As best seen in FIG. 6 a single transducer 66 is shown at two different positions. These positions are indicated by the numerals 120 and 130 respectively. Still further the partially completed weld 14 is shown to have an upper level, 131 and a lower level, 132. The upper and lower levels of the partially completed weld are selected to match the given welding pass being inspected. The pulse/echo data of the respective transducers 66 are then taken from the region bounded by the two ultrasonic beams shown in FIG. 6. It should be appreciated that the transducer 66 on the opposite side of the weld 14 inspects a similar area on the opposite side of the weld 14. In this arrangement the location and source of a predetermined echo is determined from the geometry. For example, ultrasonic reflections may be observed from the top corner 133, and from the very top surface 134 of the partially completed weld 14. These may be caused by LOF; porosity; and from roughness around the root. The ultrasonic echoes of interest are of course those resulting from LOF and from porosity problems. The LOF echoes come from the region of the partially completed weld below the top surface 134. Generally these echoes have a substantially elevated level. Ultrasonic echoes due to porosity are at a much lower signal level, and come from anywhere in the weld region below the top surface 134 thereof. Still further porosity near the side wall of the weld 14 is distinguished from LOF by examining the echo signal pattern to see if it has a pattern similar to that displayed by porosity.

Cover Pass

As best seen by a study of FIG. 7 the apparatus 10 which implements the method of the present invention is shown in an arrangement to detect a weld defect such as a lack of fusion (LOF) in the cover pass region 135 of a weld 14 which has just been completed. In this arrangement, the ultrasonic beam produced by the transducer 66 is positioned to intersect the top surface 141. As seen in FIG. 7, an LOF 142 will cause a reflection earlier in time than the echo from the top surface 141. This echo will have to be discriminated from echoes from the edge 143 of the cover pass and which may occur at approximately the same point in time. As a general matter the LOF signal will be generally larger in magnitude than that produced from the other location.

As noted above, the apparatus 10 which implements the methodology of the present invention includes a controlling computer 90 having executable programming 200 which controls the pair of pulser/receivers 93 and which in turn are electrically coupled with each of the transducers 66. The controlling computer 90 further has an analog to digital converter 100 which receives the ultrasonic signal which passes through or is reflected from the partially completed weld 14 being inspected. Yet further the controlling computer 90 has an analog and digital input/output assembly 110 which is coupled in signal transmitting relation relative to the pair of pulsers/receivers 93. This analog and digital input/output assembly 110 generates a signal causing the pair of pulsers/receivers 93 to produce a pulse and wherein this pulse further causes the analog to digital converter 100 to receive the resulting ultrasonic signal.

As seen in FIGS. 3 and 4, the step of pulsing the respective transducers 66 occurs at a plurality of predetermined locations 150 along the path of travel 60. Controlling computer 90, by means of the executable programming 200 determines the predetermined locations. As can be seen in FIG. 4, and as discussed above, the partially completed weld 14 is formed by multiple passes of a movable welding assembly 11, and wherein the respective paths of travel 60 of the individual transducers 66 are in phase when utilized to detect welding defects which occur in the root pass 117 of the partially completed weld 14. Still further and as seen in FIG. 3 the respective paths of travel 60 of the individual transducers 66 are out-of-phase when utilized to detect defects in the root 117, hot and fill 118 and cover pass 135 of the partially completed weld 14.

The present invention contemplates that the analysis of the ultrasonic signals occurs following the completion of the movement along the respective first and second components 61 and 62 of the individual paths of travel 60. As earlier discussed, the first and second components 61 and 62 are defined between second position 64 and first position 63 and between first position 63 and second position 64, respectively. Consequently, ultrasonic signal analysis takes place following completion of the movement of the respective transducers between the first to the second position, and the second to the first position, respectively. Still further, it should be understood that the respective transducers 66 may be operated in pitch/catch mode to inspect the root pass 117 of the partially completed weld 14. However, the transducers 66 may also be operated in a pulse/echo mode to inspect the root 117, hot and fill 118 and cover pass 135 of the partially completed weld 14.

Executable Programming

Figure 8:
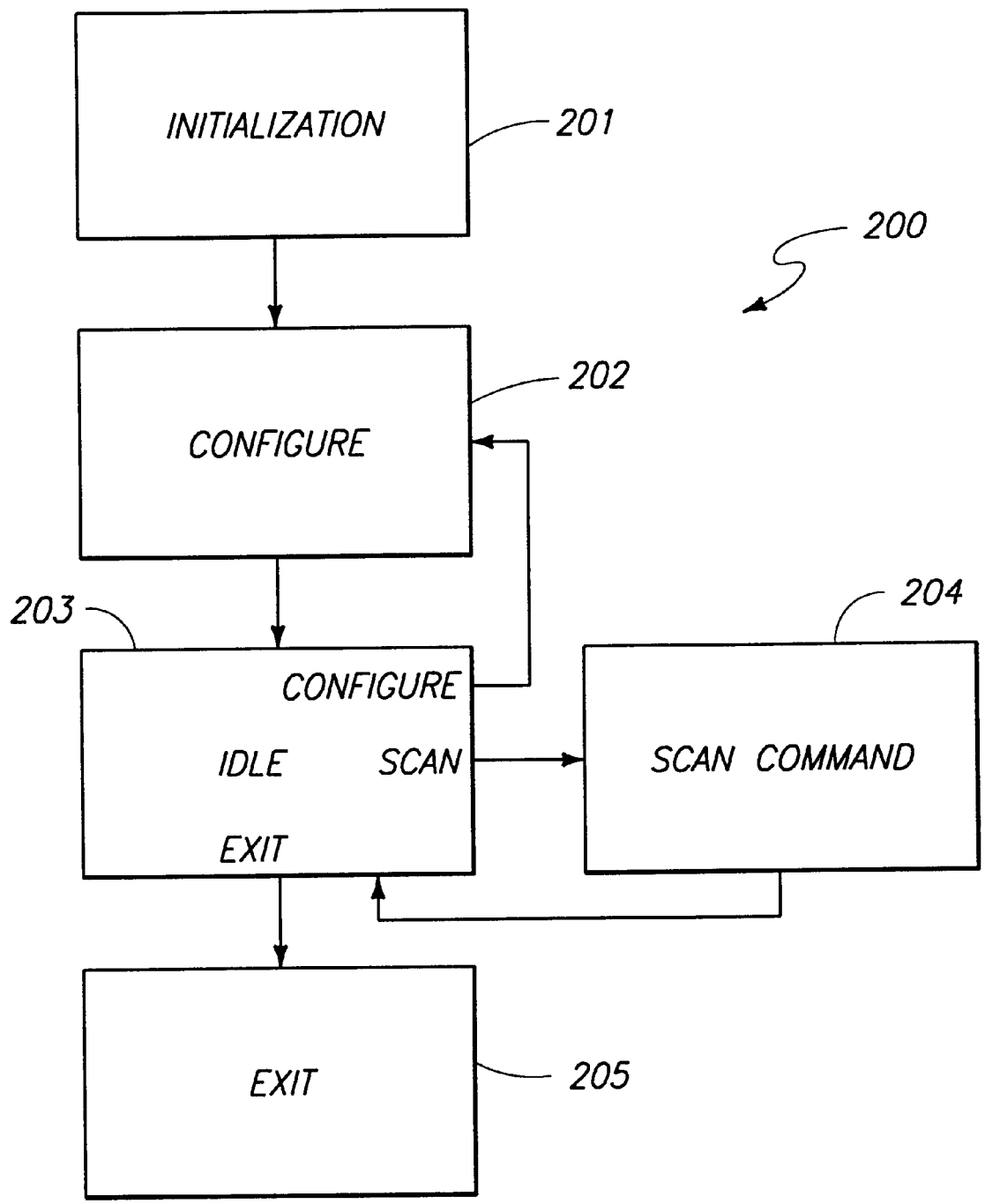
FIG. 8 is a high level block diagram of a computer system which is suitable for implementing the methodologies of the present invention.

As has been discussed briefly, above, controlling computer 90 employs executable programming 200 generally which is indicated by the numeral 200 and shown generally at FIG. 8. The executable programming 200 generates and thereafter analyzes the ultrasonic signals which are reflected from, or pass through the partially completed weld 14 that is to be inspected. FIG. 8 shows a high level organizational schematic of the executable programming 200. In this regard, the high level organizational schematic shows an Initialization subroutine 201 which is coupled with a Configure subroutine 202. Still further, the high level organizational schematic shows an Idle subroutine 203 which is further coupled in loopback fashion to the Configure subroutine 202. Still further, the Idle subroutine 203 is coupled in a loopback configuration with a Scan command subroutine generally indicated by the numeral 204. The high level organizational schematic further has a subroutine for Exiting from the program 205.

Figure 9:
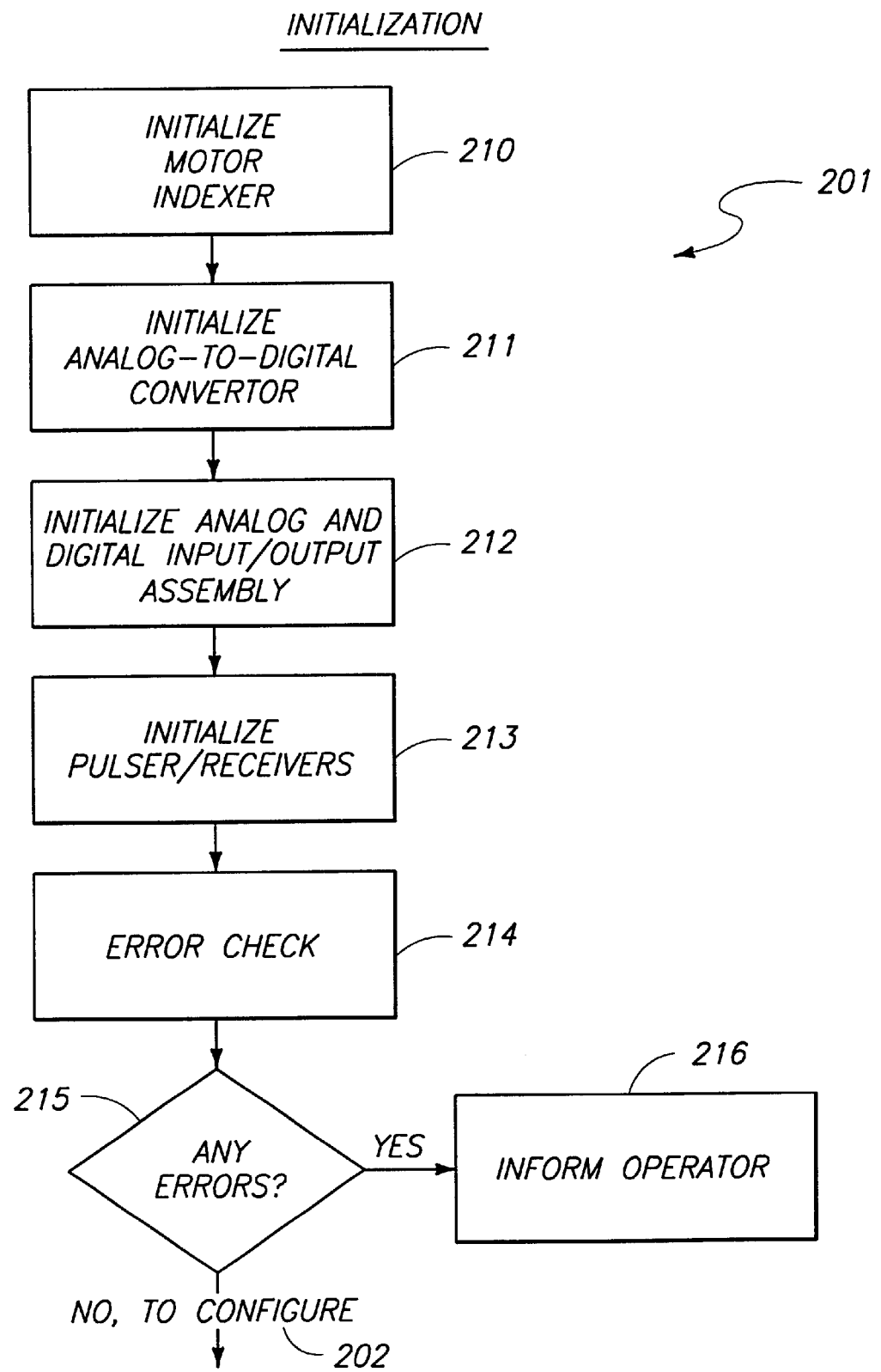
FIG. 9 is a high level organizational diagram illustrating one aspect of the present invention.

Referring now to FIG. 9, the Initialization subroutine 201 is shown in more particularity, and wherein during this subroutine, the executable programming 200 sequentially initializes the Motor Indexers 115 at 210, and thereafter initializes the analog to digital converter 100 at 211. Subsequently, the executable programming 200 initializes the analog and digital input/output assembly 110 at 212 and further initializes the pulser/receivers 93 at 213. Following this initialization an error check is performed by the executable programming 200 as indicated at 214, and the programming subsequently queries whether any errors 215 have been detected. If errors are detected, the executable programming is operable to inform the operator of such errors 216. The initialization subroutine 201 then provides its output to the Configure subroutine 202 which is shown in more particularity in FIG. 10.

Figure 10:
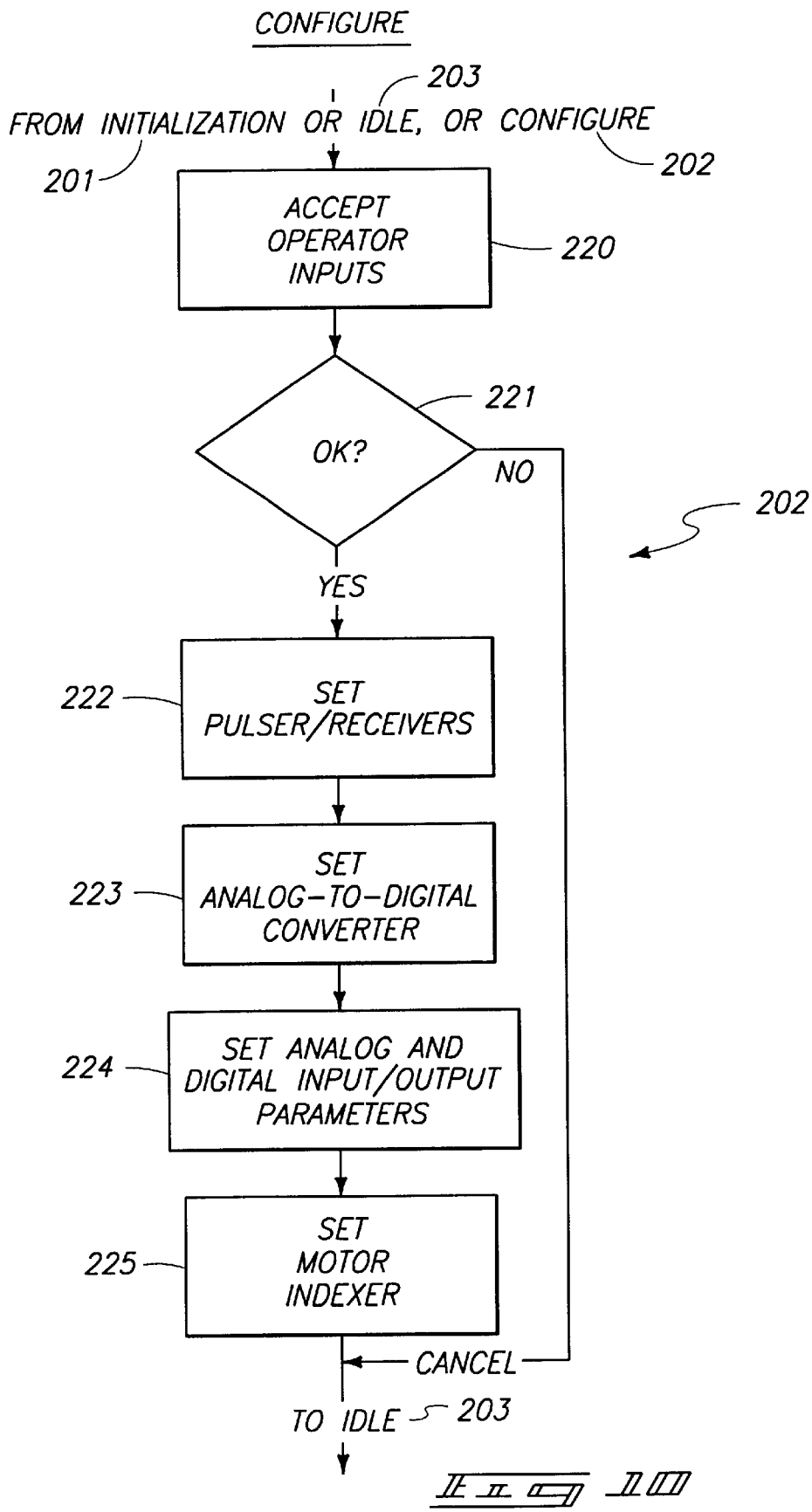
FIG. 10 is a flow diagram illustrating certain methodical aspects of the present invention.

As seen in FIG. 10, the Configure subroutine 202 is shown with greater specificity. It will be seen that the Configure subroutine 202 may be accessed from the Initialization subroutine 201 or Idle subroutine 203. Upon initiation of this subroutine the operator has the opportunity to modify some of the operating parameters of the apparatus 10, at step 220. The operator may then request the enabling computer programming 200 to accept (OK) or ignore the modifications. The enabling computer programming 200 then will accept operator input 220. This query 221, if in the affirmative, will allow the subroutine to continue and subsequently set the pulser/receivers 93 at 222 and then subsequently the analog to digital converter 100 at 223. Still further subsequent to setting the analog to digital converter 100, the subroutine will then set the analog and digital input/output assembly 110 parameters at 224. This will subsequently cause the executable programming 200 to set the motor indexer 115 as appropriate at step 225. If the query to accept the operator input 220 is in the negative, the subroutine returns to the Idle subroutine 203 as shown.

Figure 11:
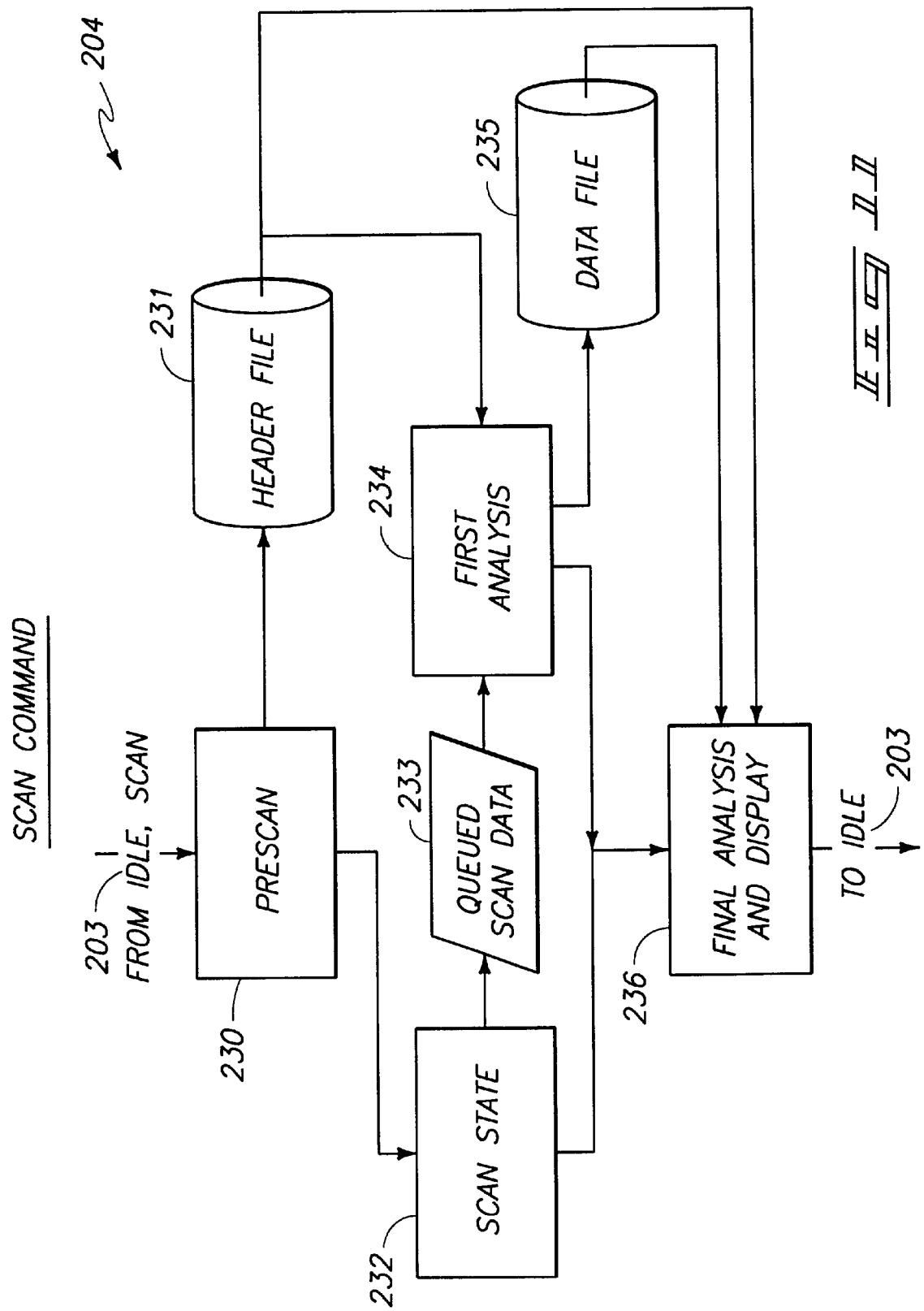
FIG. 11 is a high level block diagram illustrating one aspect of the present invention.

As best seen in FIG. 11, the Scan Command, which is generally indicated by the numeral 204 in FIG. 8, is shown with more particularity. FIG. 11 is a high level organizational schematic regarding this particular subroutine of the enabling computer programming 200. In this regard, the Scan Command 204 implements a Pre-Scan subroutine 230 which will be discussed in further detail below. Still further, and following Pre-Scan, data from the Pre-Scan 230 is received into a Header File 231 which is subsequently shared at a later point in the analysis. Still further, the Scan Command 204 has a Scan State subroutine 232 which produces scanning data 233 which is then queued for a first analysis which is conducted at 234. Subsequent to the First Analysis 234, the data is placed in a Data File 235 and a Final Analysis and Display is conducted by the enabling computer programming 200 at a further subroutine 236 which will also be discussed below. Following this final analysis and display 236 the enabling computer program 200 returns to the Idle subroutine 203.

Figure 12:
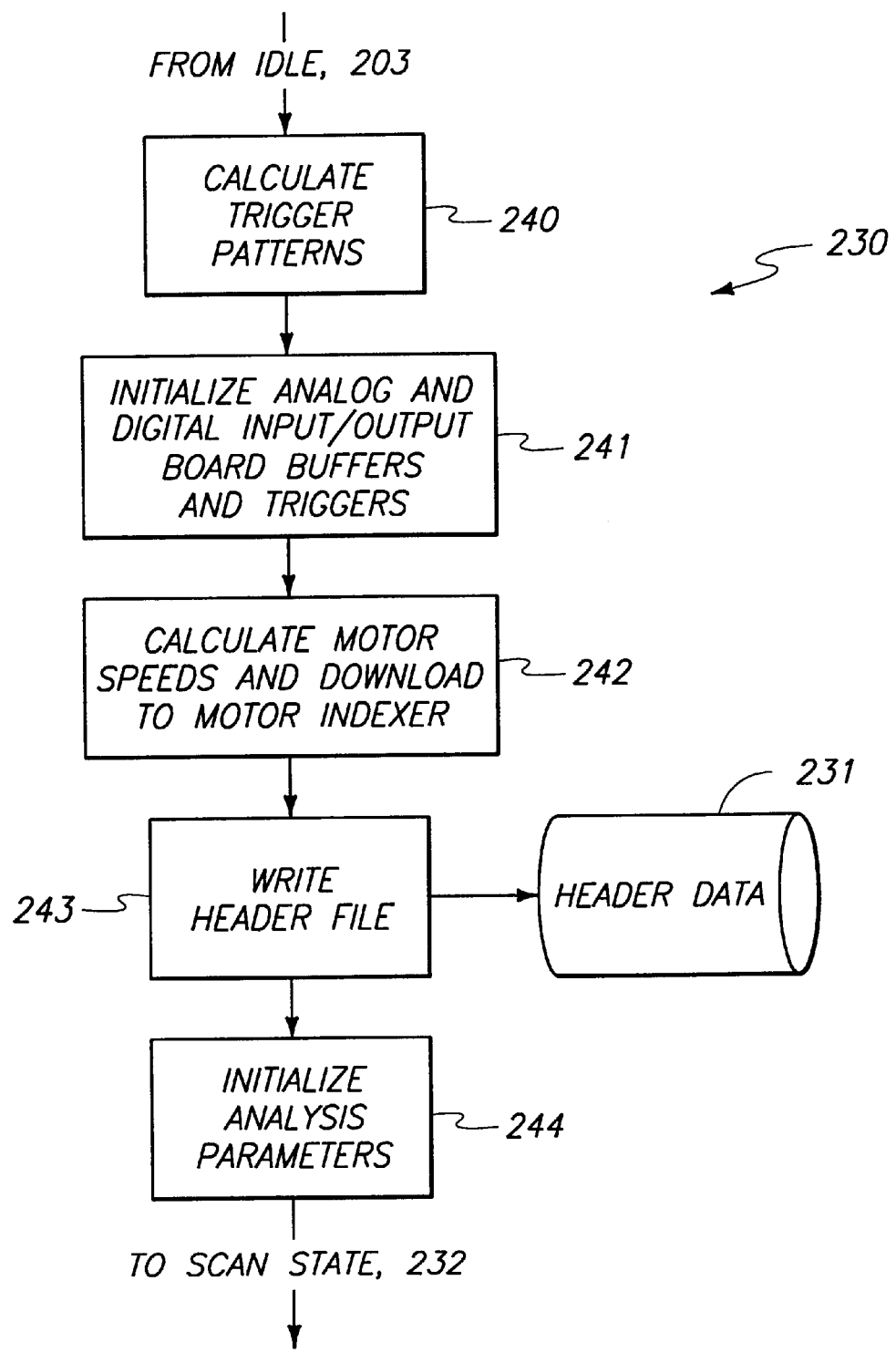
FIG. 12 is a flow diagram illustrating certain methodical aspects of the present invention.

As best seen by reference to FIG. 12, the Pre-Scan subroutine 230, and which was first identified in FIG. 11, is shown in more particularity. As will be seen in that view from the Idle subroutine 203, data is subsequently processed during the Pre-Scan subroutine 230 to calculate, at a first step the Trigger Patterns 240. Subsequently, the computer programming 200 initializes the Analog and Digital Input/Output Board Assembly 110 Buffers and associated Triggers 241. Thereafter, the programming in this subroutine Calculates the Motor Speeds and Downloads that information to the Motor Indexers 115 at step 242. Thereafter, operational data for the configuration of apparatus 10 is written to the header file at step 243, and then delivered to the Header File 231 as shown in FIG. 12. This header data includes information about the movable welder 11, the partially completed weld 14, the substrate 20, the paths of travel 60, the transducer 66, the pulser/receiver 93, the analog to digital converter 100, and the analog and digital input/output assembly 110. Following the writing to the Header File 231 at step 243, the Pre-Scan subroutine 230 Initializes Analysis Parameters 244 for analyzing and displaying the scan data. The subroutine then returns to the Scan State 232 which is set forth in more particularity in FIG. 13.

Figure 13:
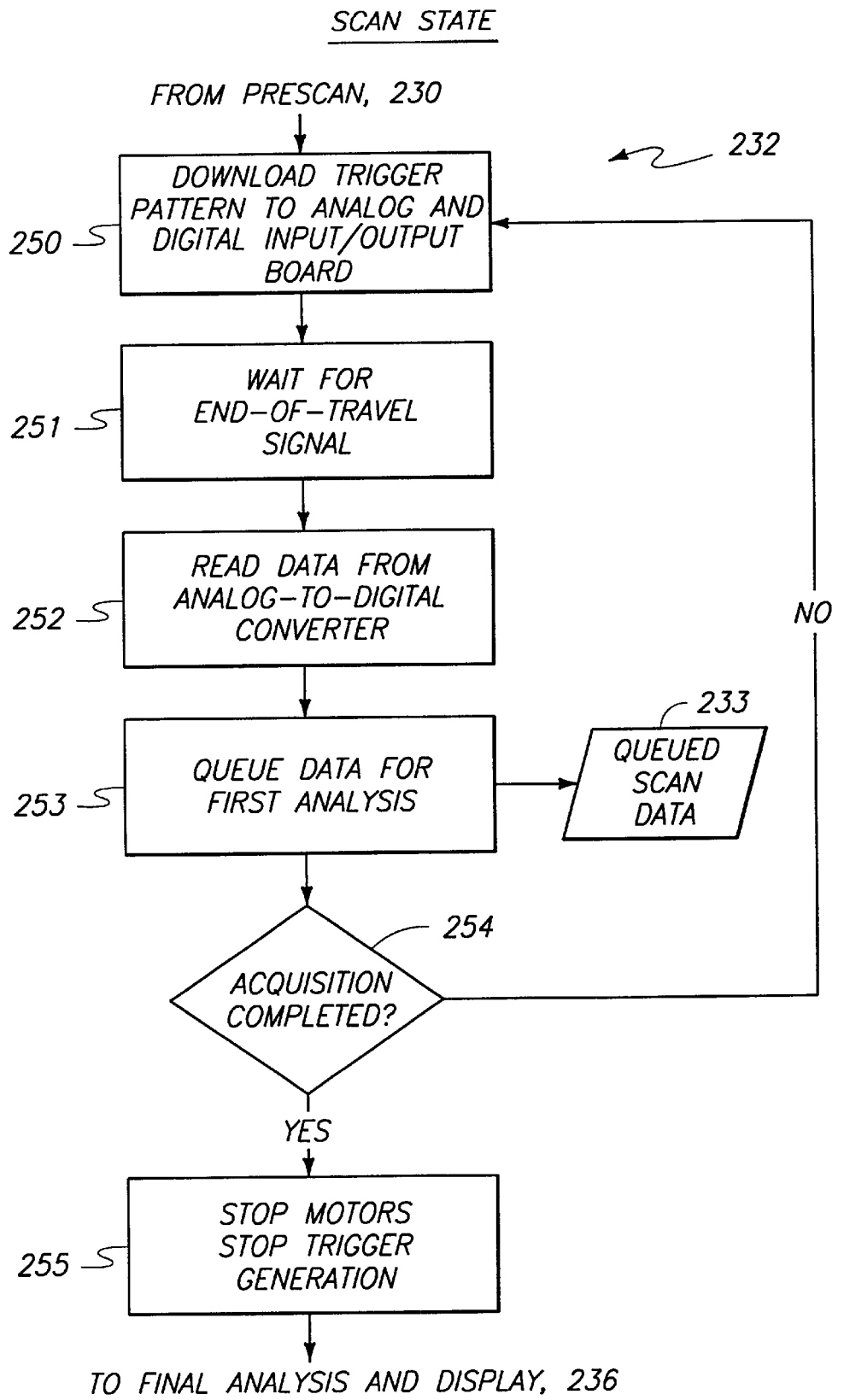
FIG. 13 is a flow diagram illustrating certain methodical aspects of the present invention.

Referring now to FIG. 13, the Scan-State subroutine 232 earlier depicted in the high level schematic diagram shown in FIG. 11 is set forth with a higher degree of particularity. In this regard, the implementing executable programming 200 proceeds to download a given Trigger Pattern to the analog and digital input/output assembly 10 at step 250. Subsequent to this step, the programming waits for an End of Travel Signal at step 251 sent out by the motor indexer 115 whenever the transducer 66 reaches first position 63 or second position 64. Thereafter the programming 200 reads data from the analog to digital converter 100 at step 252. Subsequent to this step, the collected data is sent to the Queued Scan Data subroutine 233 at step 253 as shown in FIG. 13. This data consists of all the ultrasonic pitch-catch and pulseecho data acquired by transducers 66 at predetermined transducer locations 150 on either path 61 or path 62. The Queued Scan Data 233 is a queue that is subsequently available to the First Analysis 234. The computer programming 200 thereafter queries whether data acquisition has been completed at step 254 and, if not, the Downloaded Trigger Pattern routine set forth in step 250 begins again The acquisition may be complete when a particular pass of the partial weld 14 is complete or when the operator interrupts the process. If acquisition has been completed, the programming 200 implements a command to stop the Motors and Stop Trigger Generation at step 255. The computer programming 200 then moves on to the Final Analysis and Display subroutine 236 as seen in FIG. 11.

Figure 14:
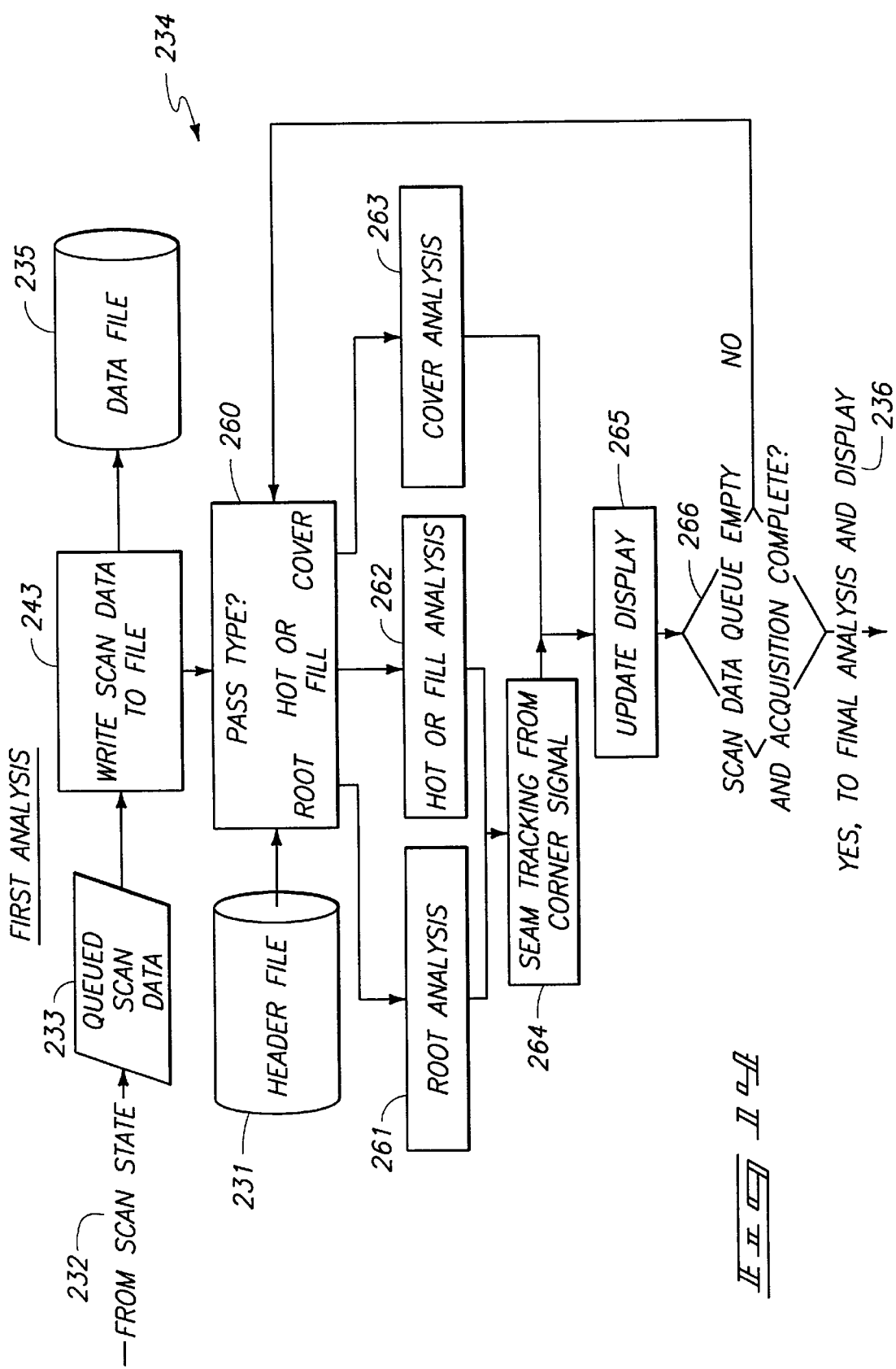
FIG. 14 is a flow diagram illustrating certain methodical aspects of the present invention.

Referring now to FIG. 14, the First Analysis subroutine 234 is shown with more particularity. As will be seen, whenever data are available in the Queued Scan Data 233, the steps in the First Analysis subroutine 234 will be executed. One set of pitch-catch and pulse-echo data acquired at the predetermined transducer locations 150 on either path 61 or path 62 are read from the queue 233 and are written to a data file 235 for final analysis and display 236 and archiving in step 259. The programming 200 obtains the operational parameters from Header File 231. The programming 200 queries the Header File 231 regarding the pass type 260, that is whether it is a root pass 117; hot and fill pass 118; or cover pass 135 which is being analyzed. Subsequently using the data from the queued scan data 233 the respective subroutines for the root analysis 261; hot or fill analysis 262; or cover analysis 263 are implemented. Still further, this Analysis subroutine 234 includes a Seam Tracking and Corner Signal analysis at step 264. The data generated at these steps is then later supplied into an Updated Display which is shown at step 265. The executable programming 200 implements a query regarding whether the Scan Data Queue 233 is Empty and whether acquisition is complete. If response to this query is in the negative, the programming loops back and begins the analysis again at step 259 obtaining the next data set from the queue 233 and writing the data to the data file 235. However, if this response is in the affirmative, the subroutine continues to the Final Analysis and Display step which was earlier discussed with respect to numeral 236.

Figure 15:
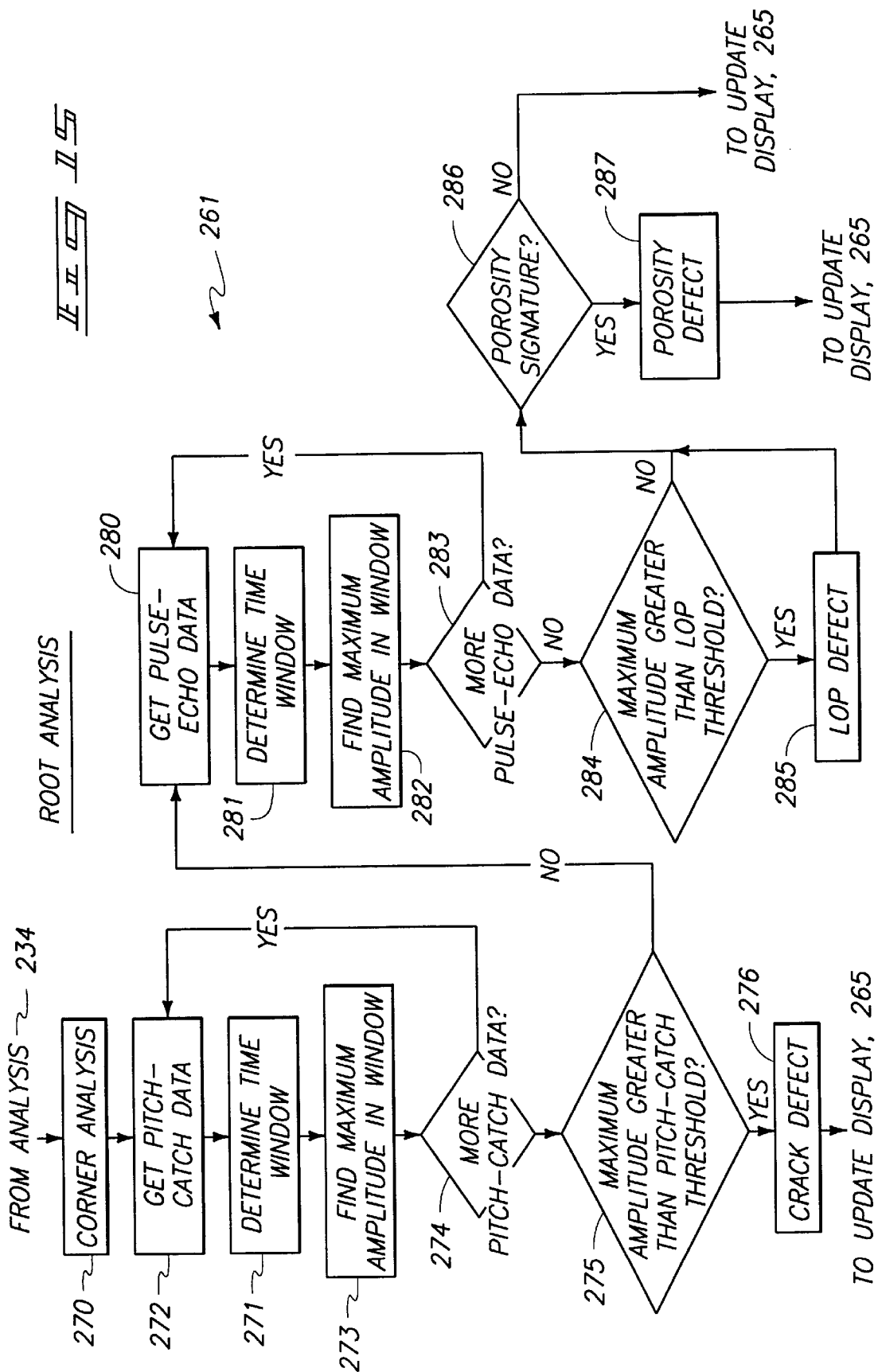
FIG. 15 is a flow diagram illustrating certain methodical aspects of the present invention.

Referring now to FIG. 15 where the Root Analysis subroutine is shown with more particularity, it will be seen that from the First Analysis subroutine 234 that the implementing computer programming 200 performs a corner analysis at step 270, as indicated. Thereafter, the computer programming obtains Pitch-Catch data acquired at one of the predetermined transducer locations 150 at step 271, and subsequently Determines a Relevant Time Window at step 272. Consequently, the computer programming 200 determines a Maximum Amplitude in the Window at step 273; and then queries whether More Pitch-Catch Data are available from another of the predetermined transducer locations 150 at 274. If the response to this query is in the affirmative, the programming loops back to step 271, as noted above, and again acquires new pitchcatch data. If no more pitch-catch data at step 274 are available, a Maximum Amplitude of this pitch-catch data is determined and a calculation is performed to determine if this amplitude is less than the pitch-catch threshold at step 275. If this is so, then a determination that a crack exists is made at step 276. At that point, the Update Display portion of the programming at step 265 is updated to reflect the presence of the crack. As will be seen in FIG. 15 if the pitch-catch data has a maximum amplitude at step 275 which is greater than the pitch-catch threshold, then the implementing computer programming at step 280 obtains pulse-echo data that were acquired from one of the predetermined locations 150. Thereafter, the computer programming 200 Determines a Time Window and also calculates a maximum amplitude of that same window at steps 281 and 282, respectively. Thereafter, the computer programming 200 queries whether more pulse/echo data are available from another of the predetermined transducer locations 150 at step 283 and if the response to this query is in the affirmative, the programming loops back and initiates the pulse/echo data collection at step 280 again. If, however, no more pulse-echo data are available from another of the predetermined transducer locations 150, the programming queries, whether the Maximum Amplitude of the Pulse/Echo data is greater than the LOP threshold which has already been established by the programming 200. If response to this query is in the affirmative, an LOP defect is noted at step 285. If, however, this query is in the negative, the computer queries whether a porosity signature 286 is present. If a porosity signature is present, a porosity defect is indicated at step 287, and in both events, the Updated Display of step 265 is provided with the correct information regarding the defects which have been located.

Figure 16:
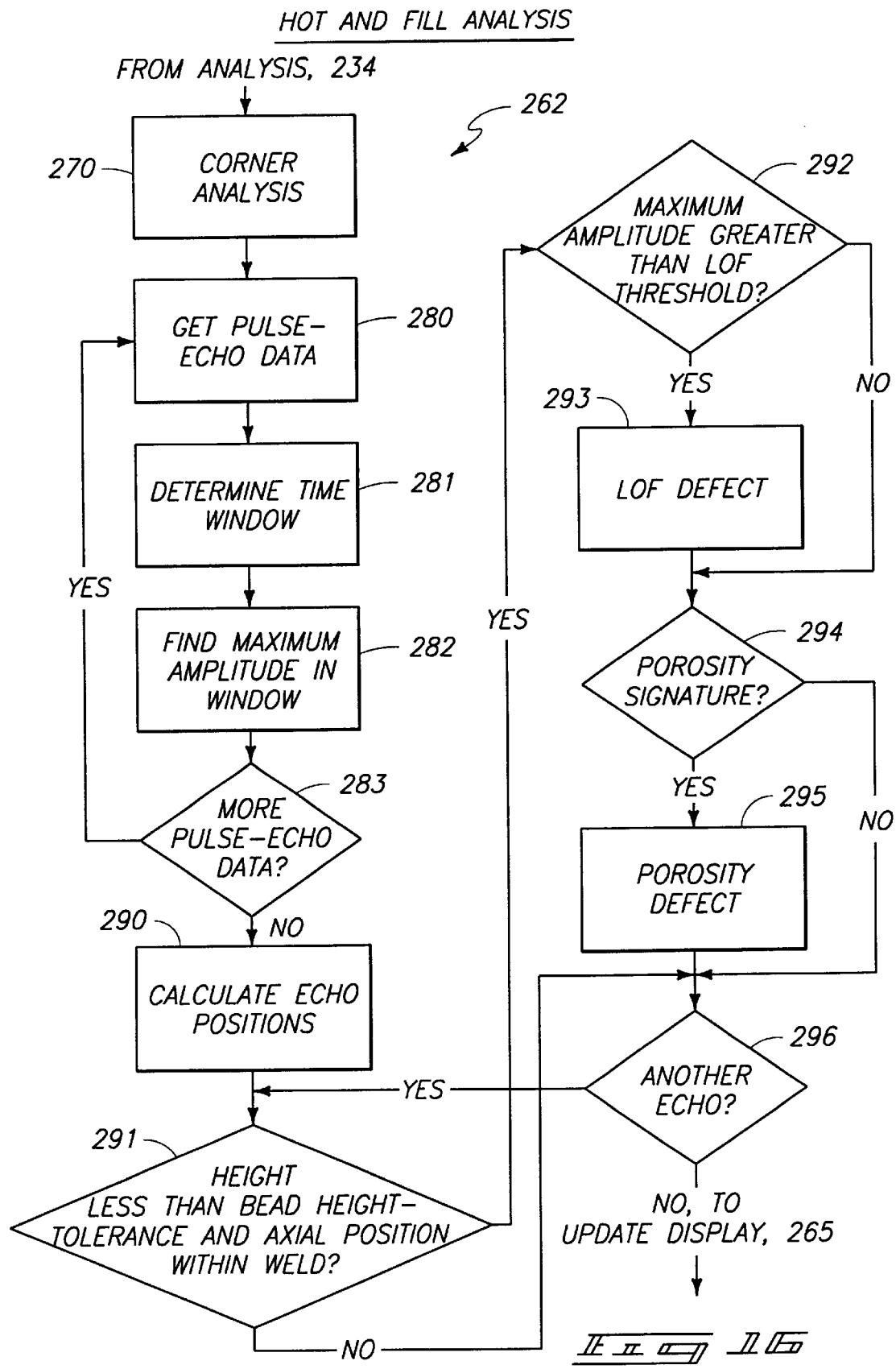
FIG. 16 is a flow diagram illustrating certain methodical aspects of the present invention.

Turning now to FIG. 16, the Hot and Fill Analysis subroutine 262 and which was first seen at FIG. 14, is now shown with more particularity. As seen in FIG. 16, data obtained from the queued scan data 233 during First Analysis 234, step 259, are obtained, and thereafter utilized in the Corner analysis subroutine 270, which will be discussed in greater detail hereinafter. As seen in FIG. 16, the executable computer programming 200 provides at step 280 a command to secure Pulse/Echo data 280. As earlier noted, upon initiation of this step, the computer programming 200 determines an appropriate Time Window at step 281, and subsequently finds a Maximum Amplitude for the Window at step 282. Thereafter, more Pulse/Echo data may be available following the query at step 283. If this is in the affirmative, the executable programming 200 loops back to step 280 and then subsequently repeats itself. However, if more Pulse/Echo data are not available, the executable programming at step 290, Calculates the Echo Position which is the height above the bottom surface 24 and the horizontal position relative to the centerline of the partially completed weld 14. This horizontal position is also known as the axial position. For example, the computer programming at step 291, will query whether the height is less than the height of the top surface of the partially completed weld 134 minus a tolerance and/or the axial position is located at or between the side walls 25 and/or Actual Position within the weld 14. If the answer to this query is in the affirmative, the computer programming will then query whether the Maximum Amplitude is greater than the LOF threshold at step 292. In the alternative, if the query to step 291 is in the negative, the computer will query at step 296 whether Another Echo is Present in this pulse-echo data. As seen, the affirmative answer to that query loops back to provide again the query found at step 291. As noted above, if the query regarding the maximum amplitude being greater than the LOF threshold 292 is in the affirmative, an LOF defect at step 293 is identified. Still further the implementing programming 200 will subsequently take this information and will query regarding whether the signal represents a porosity signature at step 294. If a porosity signature is found, a porosity defect is indicated at step 295 and, thereafter, the information regarding the Porosity Defect 295 and the LOF Defect 293 are provided to the Update Display of subroutine at step 265.

Figure 17:
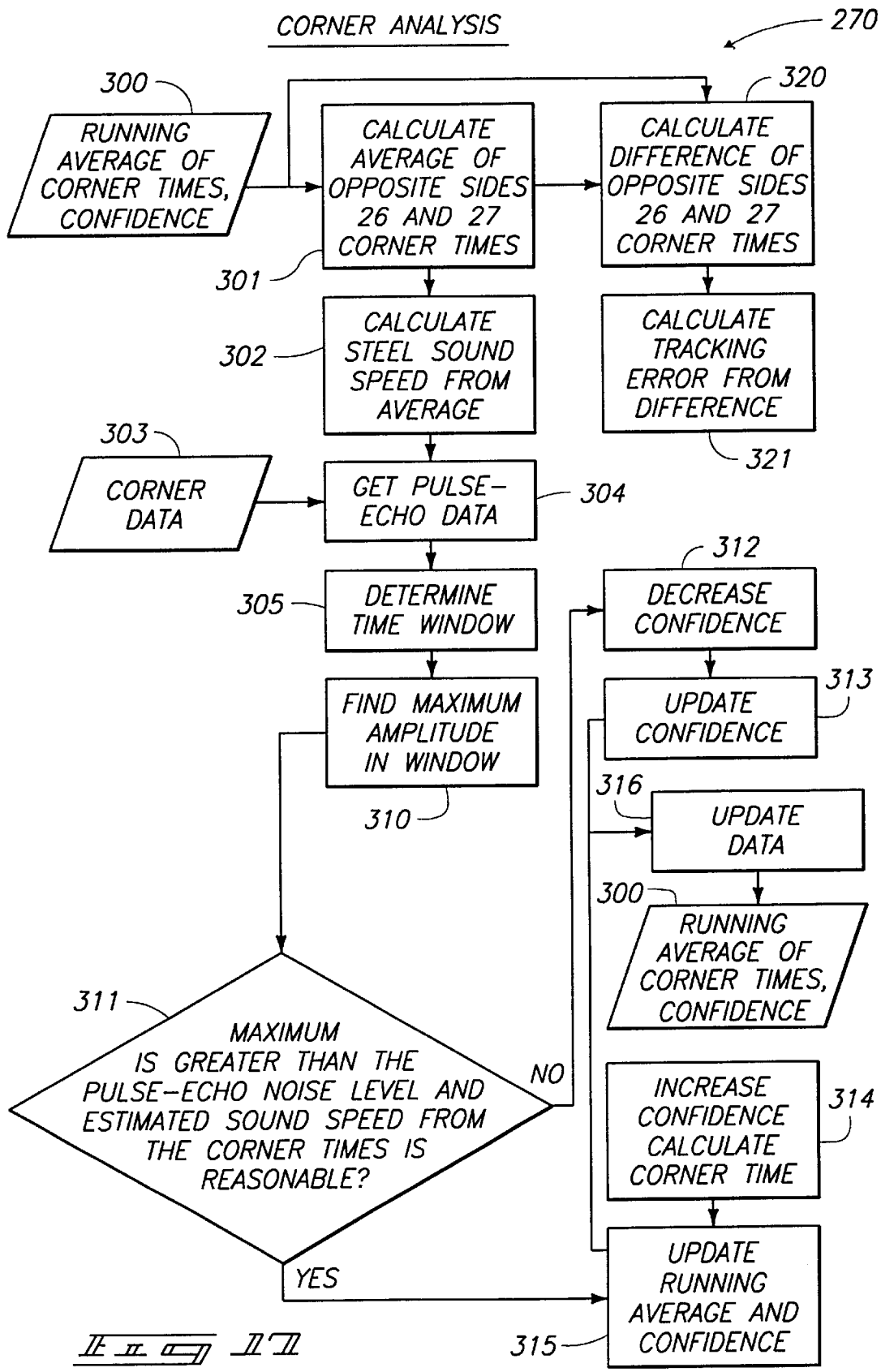
FIG. 17 is a flow diagram illustrating certain methodical aspects of the present invention.

Referring now to FIG. 17, where the corner analysis subroutine 270 is shown with some degree of particularity, it will be seen that this subroutine includes a first step of calculating a Running Average of the Corner Times and Confidence at step 300. Subsequently, this analysis is utilized in step 301 to calculate an Average of the Inboard and Outboard Corner Times where Inboard refers to data by the transducer 66 on the first opposite side 26 and Outboard refers to data taken by the transducer 66 on the second opposite side 27. Following calculation of the Inboard and Outboard Corner Times 301, the computer programming 200 calculates the speed of the sound of steel from an average at step 302. For the inspection of the root pass 117 and of the hot and fill passes 118, one of the predetermined transducer locations 150 is chosen so that the ultrasonic pulse-echo signal is from the top corner 133 of the weld preparation. This data is numbered 303. At step 304 this data is obtained from the data file 235 Subsequently, the computer programming 200 determines an appropriate Time Window at step 305, and thereafter a maximum amplitude for the given window is calculated at step 310. As seen in FIG. 17, the computer programming 200 queries whether the Maximum Amplitude of the Pulse Echo Data is greater than the Pulse/Echo Noise Level and thereafter queries whether the estimated sound speed from the inboard and outboard times is reasonable at step 311. If this query is answered in the affirmative, an update of the running average and confidence of the system is done at step 315. If this same question is answered in the negative, a Decrease in Confidence is noted at step 312, and a subsequent Update of the Confidence information is provided at step 313. As will be seen in step 314, with increasing confidence, further calculation of corner time speed is performed at step 314, and provided to update the running average and confidence at step 315. As will be seen, these calculations are provided in an Updated data stream 316 and thereby updates the running average of the corner times and confidences as originally provided for in step 300. As will be seen further in FIG. 17 at step 320, the computer programming 200 calculates the Difference of the Inboard and Outboard Corner Times, and thereafter further supplies that information at step 321, to calculate the tracking error from the difference in same.

Figure 18:
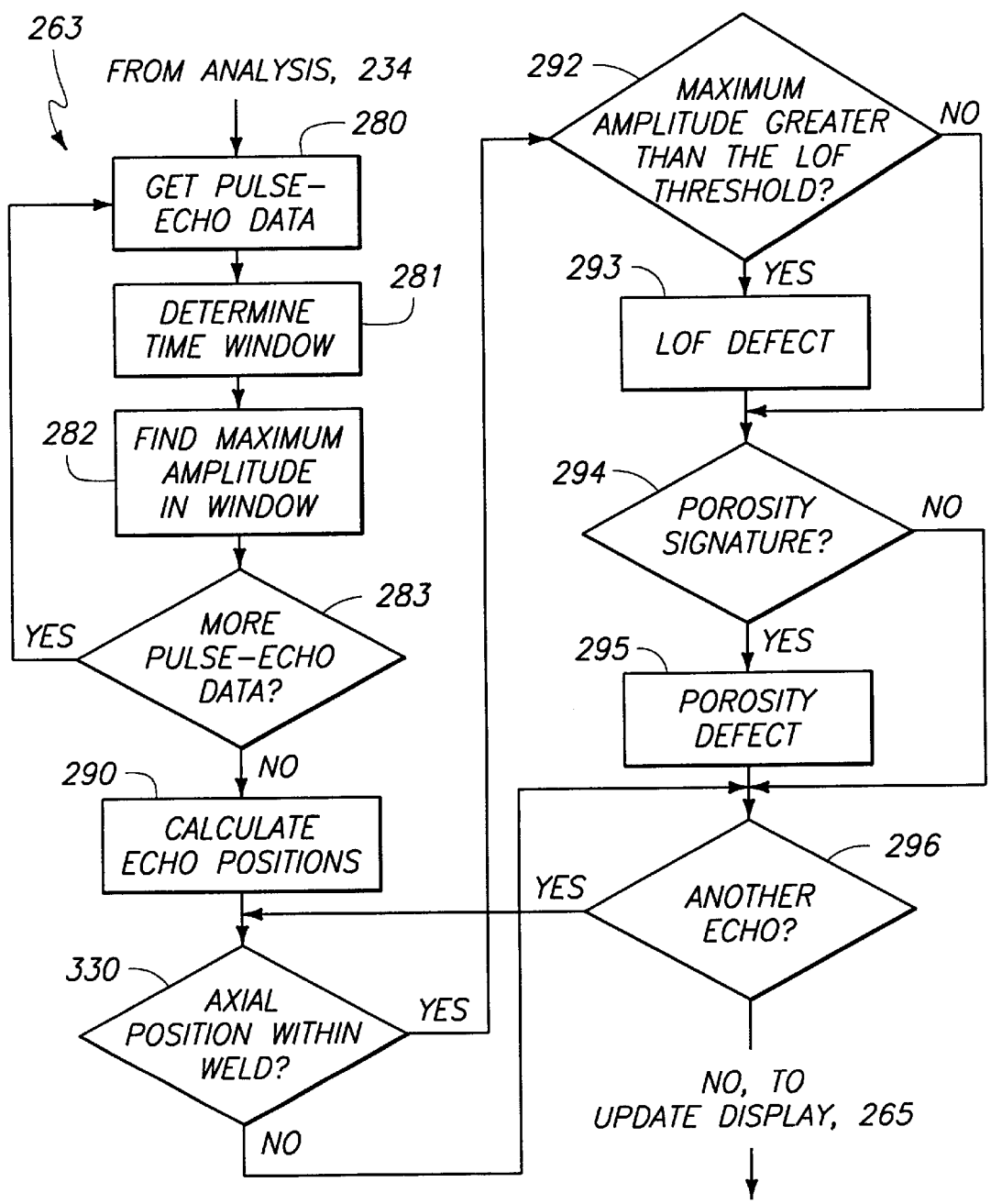
FIG. 18 is a flow diagram illustrating certain methodical aspects of the present invention.

Referring now to FIG. 18, the cover analysis subroutine 263 earlier referenced in FIG. 14 is shown with a greater degree of particularity. As will be seen following a comparison with FIG. 15, the cover analysis 263 follows an analysis that is similar to the hot and fill pass analysis 262 whereby the implementing computer programming 200 begins at step 280 to obtain pulse-echo data that were acquired from one of the predetermined transducer locations 150 and thereafter determines an appropriate time window 281. Thereafter, this programming finds a Maximum Amplitude for the same window at step 282. Subsequently, the computer programming 200 queries whether more Pulse/Echo data are available from the queued scan data 233 at another of the predetermined locations 150 at step 283. If the query at step 283 is answered in the affirmative, the computer programming 200 loops back to step 280 and obtains more Pulse/Echo data. If the query at step 283 is answered in the negative, the computer programming 200 calculates the Echo Position 290 and queries whether the echo position is axial within the weld at step 330. If the answer to this query is in the negative, the computer programming 200 asks another query regarding whether another echo is present at 296. As seen from FIG. 18, if the answer is in the negative regarding whether the echo is axial of the weld, then step 330 is again repeated. In any event, the computer programming 200 Updates the Display subroutine at step 265. As seen in FIG. 18, if the position of the echo is axially within the weld, the computer programming will query regarding whether the Maximum Amplitude of the Echo is greater than the LOF threshold 292 which has been established. If this is indeed the case, an LOF defect is thereby established at step 293, and the Updated Display is accomplished at step 265. In contrast, if an LOF defect is not identified, the computer programming 200 queries whether a Porosity Signature is present at step 294. If this is the case, a porosity defect is established at step 295, and thereafter the display is updated at step 265.

Figure 19:
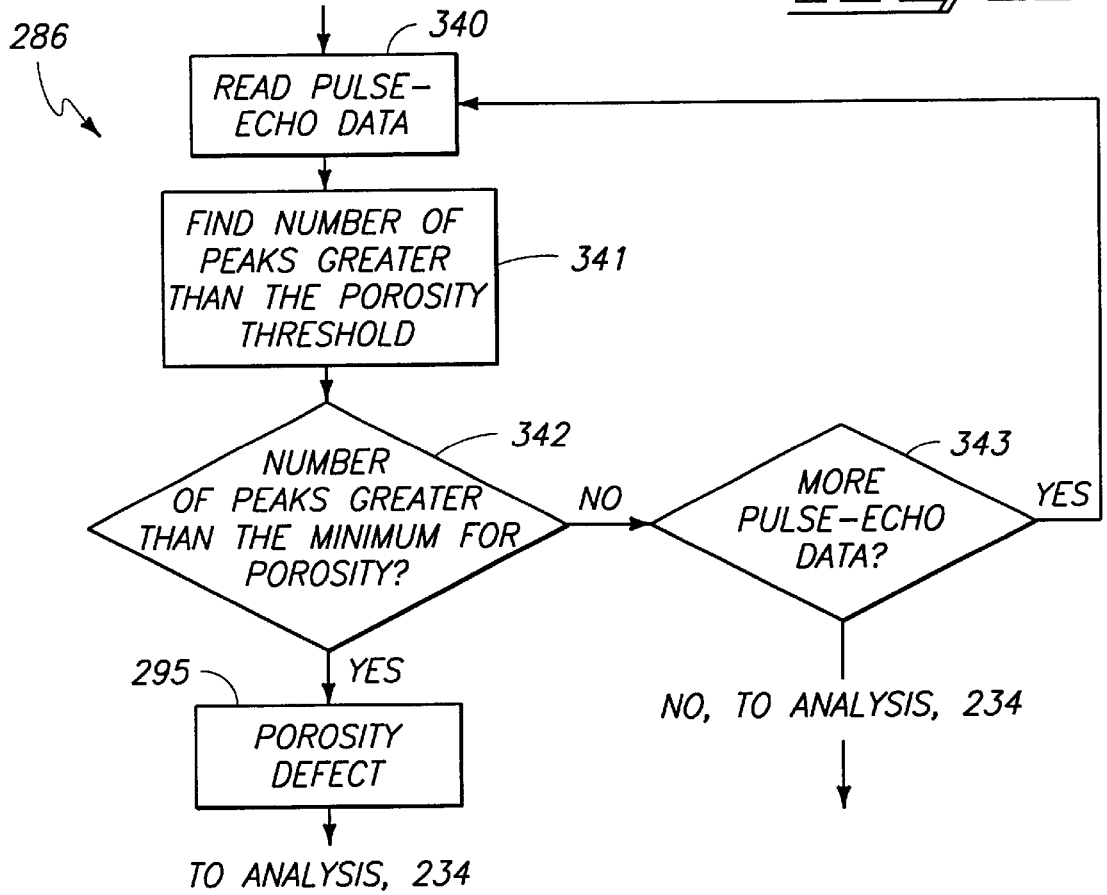
FIG. 19 is a flow diagram illustrating certain methodical aspects of the present invention.

Referring now to FIG. 19 where the earlier discussed porosity signature is processed by the computer programming 200, it will be seen that porosity signatures received from the Root; Hot and Fill; and Cover analysis subroutines 261, 262 and 263, respectively are received and subsequently processed at a Reading data step generally indicated at numeral 340. It should be understood that at step 340, data which has been collected from the predetermined scanning locations 150 along the given paths of travel 60 are provided. Porosity in the weld will provide multiple targets that will reflect ultrasound, resulting in multiple echoes in the returning data. Therefore, at step 341, the data from one pulse/echo as can, read at step 310, are analyzed to determine the number of peaks that have an amplitude that is above a given porosity threshold. At step 342, a query is made as to whether the number of peaks found in larger than the minimum required for the porosity signature. If the result of query 342 is in the affirmative, then a porosity defect is determined to be present at step 295 and the subroutine returns to the analysis subroutine 234. If the result of query 342 is negative, the computer then determines if more pulse/echo data are available from the queued scan data 233 at step 343. If the result of query 343 is negative, then the subroutine returns to the analysis subroutine 234. If the result of query 343 is in the affirmative, then the computer programming 200 goes to step 340 to read in the next available pulse/echo as can data.

Figure 20:
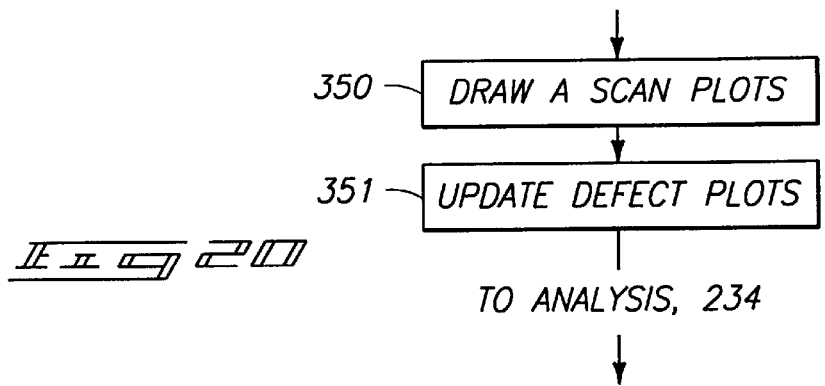
FIG. 20 is a flow diagram illustrating certain methodical aspects of the present invention.

Referring now to FIG. 20, there is shown the Update display, subroutine 265 as seen in FIG. 14. As illustrated, upon initiating this subroutine, the computer programming 200 plots the respective ultrasonic ascans that have been implemented along the path of travel 60 and which are done at step 350. Further, updated defect plots are performed at step 351. Subsequently, this subroutine returns to the First Analysis subroutine 234 as shown.

Referring now to FIG. 21, the Final Analysis and Display subroutine 236 shown in FIG. 11 is set forth with a greater degree of particularity. Whereas in the First Analysis 234 only the data from one of either the first component 61 or the second component 62 of the paths of travel are analyzed, in the First Analysis and Display 236, the entire data from the entire path of travel 60, including both components 61 and 62 over the entire length of the partially completed weld 14 are analyzed and displayed. As will be seen, the subroutine for the final analysis and display of information 236 includes the first step of reading the Header and Data files at step 360 and thereafter plotting a Scan Analysis at step 361. Thereafter, the operator can select data to analyze and plot, at step 362. Also, the executable programming 200 analyzes selected data at step 363. Thereafter, at step 364, the operator may Plot Grey Scale of Selected Data. Following this, the computer programming 200 questions at 365 whether it should return to the Idle subroutine 203. If answered in the affirmative, the executable programming returns to the subroutine indicated at step 203. Referring now to FIG. 22, Exit subroutine 205 as seen at FIG. 8 is illustrated. Upon receiving a command to exit, the computer programming 200 clears the motor indexers 115 and drivers at step 370; and further clears the analog and input/output assembly 110 drivers at step 371. Thereafter, the program 200 is rendered non-operational.

Operation

The operation of the described embodiment of the present invention is believed to be readily apparent and is briefly summarized at this point.

Figure 2:
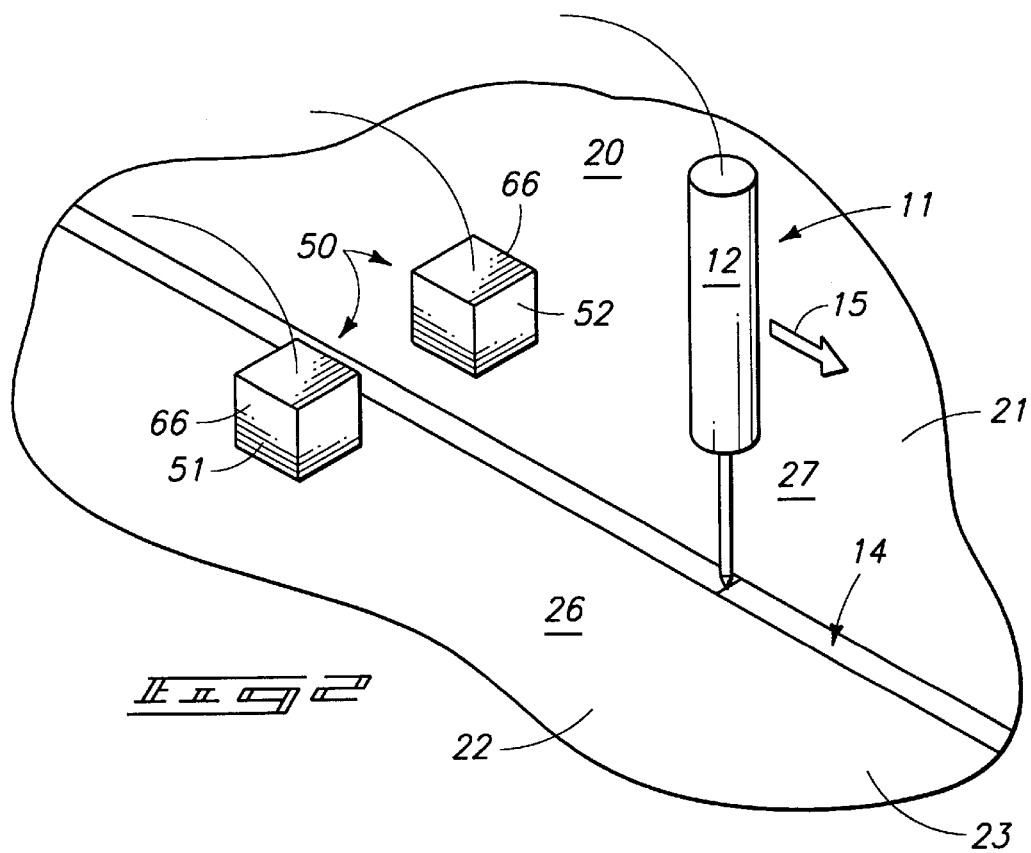
FIG. 2 is a greatly simplified view of an apparatus which implements the method of the present invention with supporting surfaces removed to show the structure thereunder.

The method for the concurrent ultrasonic inspection of partially completed welds is best seen by references to FIGS. 1 and 2. As shown therein, the method includes providing a pair of tranducers 66 which are individually positioned on the opposite sides of a partially completed weld 14 to be inspected; moving the transducers 66 along the length of and laterally inwardly and outwardly relative to the partially completed weld 14; pulsing the respective transducers 66 to produce an ultrasonic signal which passes through or is reflected from the partially completed weld; receiving from the respective transducers 66 ultrasonic signals which have passed through or are reflected from the partially completed welds 14; and analyzing the ultrasonic signal which is passed through or is reflected from the partially completed weld 14 to determine the presence of any weld defects.

As noted in the specification, the step of analyzing the ultrasonic signals is done by means of a controlling computer 90 having executable programming 200 for selectively controlling the movement of each of the motors 116. As earlier discussed, the controlling computer 90 energizes each of the motors 116 in a manner to cause the substantially synchronous movement of each of the transducers 66 along a predetermined path of travel 60 which is defined between a first and second position 63 and 64 respectively. As seen in FIGS. 3 and 4, the synchronous movement of the transducer 66 along the path of travel 60 is generally sinusoidal in shape when viewed along the length of the partially completed weld 14. Still further, the present apparatus which implements the method includes a motor indexer 115 which is responsive to the controlling computer 90 and which is disposed in signal transmitting relationship relative to the respective motors 116 and wherein the controlling computer 90 has an executable program 200 which is downloadable to the motor indexer 115 to control the motion of the respective motors 116.

The executable programming 200 employed by the controlling computer 90 directs the movement of one or more of the motors 116. If two or more motors are utilized, the motor indexer 115 directs the movement of one of the motors 116; and the other of the motors, by way of the executable program 200, substantially follows and matches the position of th e motor 116 being controlled by the executable program 200. As earlier discussed, the executable programming 200 coordinates the pulsing of the respective transducers 66 during movement of the respective transducers along their respective paths of travel 60.

As was discussed in some detail earlier, the controlling computer 90 includes a pair of pulser/receivers 93 which are controlled by the controlling computer 90 and which are individually electrically coupled with each of the transducers 66. Still further the controlling computer 90 includes an analog to digital converter 100 and which receives the ultrasonic signal which passes through or is reflected from the partially completed weld 14 being inspected. Yet further, the controlling computer 90 includes an analog and digital input/output assembly 110 which is coupled in signal transmitting relation relative to the pair of pulser/receivers 93 and which generates a signal causing the pair of pulser/receivers 93 to produce a pulse, and wherein the signal further causes the analog to digital converter 100 to receive the ultrasonic signal. As was discussed in some detail, the controlling computer 90 pulses the respective transducers 66 at a plurality of predetermined locations 150 along the path of travel 60. Controlling computer 90, of course, determines the predetermined locations 150 of these pulsed signals.

As can be appreciated from the foregoing, the method of the present invention provides a convenient means by which partially completed welds may be thoroughly inspected to determine the presence of any defects which may be immediately remedied prior to completion of the weld.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

We claim:

1. A method for the concurrent ultrasonic inspection of partially completed welds comprising:

providing a pair of transducers which are individually positioned on the opposite sides of a partially completed weld and which are substantially synchronously moveable along a predetermined path of travel which is defined between first and second positions and which is generally sinusoidal in shape when viewed along the length of the partially completed weld;

providing a pair of motors which are individually disposed in driving relation relative to each of the transducers;

providing a controlling computer having programming for selectively controlling the movement of each of the motors;

providing a motor indexer responsive to the controlling computer and which is disposed in signal transmitting relation relative to the respective motors, and wherein the controlling computer has executable programming which is downloadable to the motor indexer to control the motion of the respective motors;

moving the transducers along the length of, and inwardly and outwardly relative to the partially completed weld and along the path of travel;

pulsing the respective transducers to produce an ultrasonic signal which passes through or is reflected from the partially completed weld; and analyzing the ultrasonic signal which has passed through or is reflected from the partially completed weld to determine the presence of any weld defects.

2. A method as claimed in claim 1, wherein the executable program downloadable to the motor indexer directs the movement of one of the motors; and the other of the motors, by way of the executable program, substantially follows and matches the position of the motor being controlled by the executable program.

3. A method as claimed in claim 2, wherein the path of travel is defined between a first position where the respective transducers are nearest to the partially completed weld, and a second position, where the respective transducers are farthest away from the partially completed weld, and wherein the executable program causes the motor indexer to transmit a digital signal to the controlling computer when the respective transducers are at the second position.

4. A method as claimed in claim 3, wherein the executable program coordinates the pulsing of the respective transducers during movement of the respective transducers along the path of travel.

5. A method as claimed in claim 3, wherein the executable program coordinates the analysis of the ultrasonic signal with the movement of the respective transducers along the path of travel.

6. A method as claimed in claim 3, wherein the controlling computer further comprises:

a pair of pulser/receivers which are controlled by the controlling computer, and which are individually electrically coupled with each of the transducers;

an analog to digital converter controlled by the controlling computer and which receives the ultrasonic signal which passes through or is reflected from the partially completed weld being inspected; and an analog and digital input/output assembly controlled by the controlling computer and which is coupled in signal transmitting relation relative to the pair of pulser/receivers and which generates a signal causing the pair of pulser/receivers to produce a pulse, and wherein the signal further causes the analog and digital converter to receive the ultrasonic signal.

7. A method as claimed in claim 6, wherein the step of pulsing the respective transducers occurs at a plurality of predetermined locations along the path of travel, and wherein the controlling computer determines the predetermined locations.

8. A method as claimed in claim 7, wherein the partially completed weld is formed by multiple passes of a moveable welding assembly, and wherein the respective paths of travel of the individual transducers are in phase when utilized to detect defects which occur in the root pass of the partially completed weld.

9. A method as claimed in claim 8, wherein the respective transducers are operated in a pitch/catch mode to inspect the root pass of the partially completed weld.

10. A method as claimed in claim 7, wherein the partially completed weld is formed by multiple passes of a moveable welding assembly, and wherein the respective paths of travel of the individual transducers are out of phase when utilized to detect defects in the root, hot, fill and cover pass of the partially completed weld.

11. A method as claimed in claim 10, wherein the respective transducers are operated in a pulse/echo mode to inspect the root, hot, fill, and cover pass of the partially completed weld.

12. A method as claimed in claim 7, wherein the step of analyzing the ultrasonic signal occurs following the completion of the movement of the respective transducers from the first to the second position, and the second to the first position, respectively.

13. A method for the concurrent ultrasonic inspection of partially completed welds, comprising:

providing a pair of transducers which are individually positioned on the opposite sides of a partially completed weld which is to be inspected;

providing a pair of motors which are individually disposed in driving relation relative to each of the transducers;

providing a controlling computer having executable programming for selectively controlling the movement of each of the motors;

providing a motor indexer responsive to the controlling computer and which is disposed in signal transmitting relation relative to the respective motors, and wherein the controlling computer comprises an executable program which is downloadable to the motor indexer to control the motion of the respective motors;

energizing the respective motors with the controlling computer to cause the respective transducers to travel in a predetermined synchronous pattern of motion;

pulsing the respective transducers with the controlling computer to produce an ultrasonic signal which is reflected from, or which passes through the weld which is being inspected while the transducers are being moved in the predetermined synchronous pattern of motion; and analyzing the ultrasonic signal which is reflected from, or which passes through the partially completed weld by the controlling computer to determine the presence of any weld defects.

14. A method as claimed in claim 13, wherein the executable program downloadable to the motor indexer directs the movement of one of the motors, and the other of the motors, by way of the executable program, substantially follows and matches the position of the motor being controlled by the executable program.

15. A method as claimed in claim 14, wherein the respective transducers move along a path of travel which is generally sinusoidal in shape, and wherein the path of travel is defined between a first position where the respective transducers are nearest to the partially completed weld, and a second position, where the respective transducers are farthest away from the partially completed weld, and wherein the executable program causes the motor indexer to transmit a digital signal to the controlling computer when the respective transducers are at the second position.

16. A method as claimed in claim 15, wherein the executable program coordinates the pulsing of the respective transducers during movement of the respective transducers along the path of travel.

17. A method as claimed in claim 16, wherein the executable program coordinates the analysis of the ultrasonic signal with the movement of the respective transducers along the path of travel.

18. A method as claimed in claim 17, wherein the controlling computer further comprises:

a pair of pulser/receivers which are controlled by the controlling computer, and which are individually electrically coupled with each of the transducers;

an analog to digital converter which receives the ultrasonic signal which passes through or is reflected from the partially completed weld being inspected; and an analog and digital input/output assembly which is coupled in signal transmitting relation relative to the pair of pulser/receivers and which generates a signal causing the pair of pulser/receivers to produce a pulse, and wherein the signal further causes the analog and digital converter to receive the ultrasonic signal.

19. A method as claimed in claim 18, wherein the step of pulsing the respective transducer occurs at a plurality of predetermined locations along the path of travel as determined by the controlling computer.

20. A method as claimed in claim 19, wherein the partially completed weld is formed by multiple passes of a moveable welding assembly, and wherein the respective paths of travel of the individual transducers are in phase when utilized to detect defects which occur in the root pass of the partially completed weld.

21. A method as claimed in claim 20, wherein the respective transducers are operated in a pitch/catch mode to inspect the root pass of the partially completed weld.

22. A method as claimed in claim 19, wherein the partially completed weld is formed by multiple passes of a moveable welding assembly, and wherein the respective paths of travel of the individual transducers are out of phase when utilized to detect defects in the root, hot, fill and cover pass of the partially completed weld.

23. A method as claimed in claim 22, wherein the respective transducers are operated in a pulse/echo mode to inspect the root, hot, fill, and cover pass of the partially completed weld.

24. A method as claimed in claim 19, wherein the step of analyzing the ultrasonic signal occurs following the completion of the movement of the respective transducers from the first to the second position, and the second to the first positions, respectively.

25. A method for concurrent inspection of partially completed welds, comprising:
providing a transducer positioned on one side of a partially completed weld to be inspected;
providing a motor disposed in driving relation relative to the transducer to move it inwardly and outwardly relative to the partially completed weld;
providing a controlling computer having programming for selectively controlling the movement of the motor; and
providing a motor indexer responsive to the controlling computer, and which is disposed in signal transmitting relation relative to the motor, and wherein the controlling computer has an executable program which is downloadable to the motor indexer to control motion of the motor, and the subsequent movement of the transducer.

26. A method as claimed in claim 25, and further comprising:
pulsing the transducer to produce an ultrasonic which passes through or is reflected from the partially completed weld.

27. A method as claimed in claim 26, and further comprising:
receiving from the transducer ultrasonic signals which are reflected from the partially completed weld.

28. A method as claimed in claim 27, and further comprising:
analyzing the ultrasonic signal which has been reflected from the partially completed weld to determine the presence of any weld defects.

* * * * *